United States Patent
Chen et al.

(10) Patent No.: US 7,794,710 B2
(45) Date of Patent: Sep. 14, 2010

(54) METHODS OF ENHANCING T CELL RESPONSIVENESS

(75) Inventors: Lieping Chen, Rochester, MN (US); Scott E. Strome, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 308 days.

(21) Appl. No.: 10/127,282

(22) Filed: Apr. 22, 2002

(65) Prior Publication Data

US 2003/0039653 A1 Feb. 27, 2003

Related U.S. Application Data

(60) Provisional application No. 60/285,137, filed on Apr. 20, 2001.

(51) Int. Cl.
 *A61K 39/395* (2006.01)
(52) U.S. Cl. .................................. 424/130.1
(58) Field of Classification Search ............. 424/130.1, 424/141.1, 144.1, 154.1; 530/387.1, 388.1, 530/388.22, 388.75; 435/375
See application file for complete search history.

(56) References Cited

U.S. PATENT DOCUMENTS

| | | | |
|---|---|---|---|
| 5,580,756 A | 12/1996 | Linsley et al. | |
| 5,858,776 A | 1/1999 | Ostrand-Rosenberg et al. | |
| 6,635,750 B1 | 10/2003 | Coyle et al. | |
| 6,803,192 B1 | 10/2004 | Chen | |
| 6,808,710 B1 | 10/2004 | Wood et al. | |
| 6,891,030 B2 | 5/2005 | Chen | |
| 6,936,704 B1 | 8/2005 | Freeman | |
| 6,965,018 B2 | 11/2005 | Micksell | |
| 7,029,674 B2 | 4/2006 | Carreno | |
| 7,038,013 B2 | 5/2006 | Freeman | |
| 7,041,474 B2 | 5/2006 | Kingsbury | |
| 7,101,550 B2 * | 9/2006 | Wood et al. | 424/144.1 |
| 7,105,328 B2 | 9/2006 | Wood et al. | |
| 7,258,354 B2 | 8/2007 | Kim | |
| 7,279,567 B2 | 10/2007 | Mikesell et at | |
| 7,285,036 B2 | 10/2007 | Chang | |
| 7,358,354 B2 | 4/2008 | Mikesell et al. | |
| 7,368,531 B2 | 5/2008 | Rosen | |
| 7,368,554 B2 | 5/2008 | Mikesell et al. | |
| 7,411,051 B2 | 8/2008 | Rosen | |
| 7,414,122 B2 | 8/2008 | Fox et al | |
| 7,432,351 B1 | 10/2008 | Chen | |
| 7,449,300 B2 | 11/2008 | Chen et al. | |
| 2002/0055139 A1 | 5/2002 | Holtzman | |
| 2002/0102651 A1 | 8/2002 | Freeman et al. | |
| 2003/0044768 A1 * | 3/2003 | Wood et al. | 435/4 |
| 2005/0059051 A1 | 3/2005 | Chen | |
| 2006/0153841 A1 | 7/2006 | Freeman | |
| 2008/0213778 A1 | 9/2008 | Holtzman | |
| 2009/0274666 A1 | 11/2009 | Chen | |
| 2009/0317368 A1 | 12/2009 | Chen | |

FOREIGN PATENT DOCUMENTS

| | | |
|---|---|---|
| EP | 1456652 | 9/2004 |
| WO | WO 0107611 | 2/2001 |
| WO | WO01/14556 | 3/2001 |
| WO | WO 0114556 | 3/2001 |
| WO | WO 0200692 | 1/2002 |
| WO | WO 0200730 | 1/2002 |
| WO | WO 2007100098 | 9/2007 |

OTHER PUBLICATIONS

Dong et al., Nature Medicine, 1999, 5: 1365-1369.*
Iwai et al., Int Immunol. 2005, 17:133-144.*
Boon et al., Annu. Rev. Immunol., 2006, 24: 175-208.*
Nielsen et al., 2000, Cancer Chemother. Pharmacol., 46 (Suppl.): S62-S66.*
Lee et al., 1999, J. Immunol., 163: 6292-6300.*
Blazer et al., J. Immunol., 1996, 157: 3250-3259.*
Wilcox et al., 2009, Blood, 114: 2149 (filed by Applicant on Apr. 13, 2010).*
Brahmer et al., 2008, J. Clin. Oncol., 26 (suppl.), abstr. 3006 (filed by Applicant on Apr. 13, 2010).*
Melero et al., 2009, Clin. Cancer res., 15: 1507-1509 (filed by Applicant on Apr. 13, 2010).*
Dong et al. (1999) "B7-H1, a third member of the B7 family, co-stimulates T-cell proliferation and interleukin-10 secretion", Nature Medicine 5(12):1365-1369.
Tamura et al. (2001) "B7-H1 costimulation preferentially enhances CD28-independent T-helper cell function", Blood 97(6):1809-1816.
Freeman et al. (2000) "Engagement of the PD-1 Immunoinhibitory Receptor by a Novel B7 Family Member Leads to negative Regulation of Lymphocyte Activation" J. Exp. Med. 192(7):1027-1034.
Experimental data generated by a licensee of the present application.
Freeman, Gordan J., et al.: "Protect the killer: CTLs need defenses against the tumor" Nature Medicine 8(8): 787-789 (Aug. 2002).
Dong, Haidong, et al.: "Tumor-associated B7-H1 promotes T-cell apoptosis: A potential mechanism of immune evasion" Nature Medicine 8(8): 793-800 (Aug. 2002).
IDS submitted in U.S. Appl No. 10/890,789 concerning certain test data (submited on Nov. 6, 2007).
Bell, E. (2000) "B7h and B7-H1: new members of the B7 family", Immunology Today 21(5):59.

* cited by examiner

*Primary Examiner*—Ilia Ouspenski
(74) *Attorney, Agent, or Firm*—Millen, White, Zelano & Branigan, P.C.

(57) ABSTRACT

The invention features methods of enhancing the responsiveness of a T cell. Such methods involve interfering with the interaction between a T cell and a B7-H1 molecule.

20 Claims, 9 Drawing Sheets

SEQUENCE LISTING

<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Ile Met Asp Gln Val Pro Phe Ser Val
1               5

<210> SEQ ID NO 2
<211> LENGTH: 9

```
<212> TYPE: PRT
<213> ORGANISM: Homo sapiens

<400> SEQUENCE: 2

Ile Pro Gln Gln His Thr Gln Val Leu
 1               5

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 4
<211> LENGTH: 290
<212> TYPE: PRT
<213> ORGANISM: Mus musculus
```

-continued

```
<400> SEQUENCE: 4

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290
```

METHODS OF ENHANCING T CELL RESPONSIVENESS

This application claims benefit of U.S. provisional application No. 60/285,137, filed Apr. 20, 2001.

TECHNICAL FIELD

This invention relates to enhancing immunity, and more particularly to enhancing T cell responsiveness.

BACKGROUND

T lymphocytes are subject to various regulatory processes. It is important in some diseases (e.g., cancer) that immunosuppression mediated by disease-associated mechanisms be controlled so as to control progression of the disease.

Copending U.S. patent application Ser. Nos. 09/451,291, filed Nov. 30, 1999, and 09/649,108 filed Aug. 28, 2000, are incorporated herein by reference in their entirety.

SUMMARY

The invention is based on the discovery that B7-H1 molecules (e.g., on cancer cells) inhibit proliferation of T cells and/or apoptosis of activated T cells (CD4+ and CD8+) and thereby act as negative immunoregulatory molecules. Expression of B7-H1 by a variety of cancer cells represents a newly discovered mechanism whereby such cancer cells evade a host's immune system. The inventor has also discovered that agents that inhibit the interaction between B7-H1 and T cells reverse the negative regulatory effect of B7-H1 on T cells and thus enhance T cell responsiveness. The invention thus features methods of enhancing T cell responsiveness.

Human B7-H1 is designated hB7-H1 and mouse B7-H1 is designated mB7-H1. Where the term B7-H1 without specifying either species is used, the relevant text applies to B7-H1 molecules of any species. The hB7-H1 molecule can be the amino acid sequence as set forth in SEQ ID NO:3 and the mB7-H1 can be the amino acid sequence as set forth in SEQ ID NO:4. Also provided are fragments of SEQ ID NO:3 and SEQ ID NO:4 containing amino acid residue 20, 21, 22, 23, 24, 25, 26, 27, 28, 29, 30, 31, or 32 to amino acid residue 290 of SEQ ID NO:3 or SEQ ID NO:4.

More specifically, the invention provides a method of enhancing T cell responsiveness in a mammal. The method includes the steps of: (a) identifying a mammal with, or at risk of developing, cancer, the cells of the cancer being identified as expressing B7-H1 molecules on their surfaces; and (b) administering to the subject a compound that includes an agent that interferes with an interaction between B7-H1 and a T cell. In addition, the method can further involve administering an immunogenic stimulus to the mammal. The agent can be, for example, an antibody that binds to B7-H1, B7-H1 or a functional fragment of B7-H1, or a receptor for B7-H1 or a functional fragment of a receptor for B7-H1. The compound can be a fusion protein, e.g., a fusion protein that contains all, or part, of an immunoglobulin constant region. The cancer can be, for example, a hematological cancer, a neurological cancer, melanoma, breast cancer, lung cancer, head and neck cancer, a gastrointestinal cancer, liver cancer, pancreatic cancer, a genitourinary cancer, a bone cancer, and a vascular cancer and the mammal can be, for example, a human.

The invention also embodies a method of enhancing the responsiveness of a T cell. The method involves culturing, together, a T cell, a cancer cell identified as expressing B7-H1, and a compound comprising an agent that interferes with an interaction between B7-H1 and a T cell. The cultures can optionally also include an immunogenic stimulus. The agent can any of those listed above and the cancer cell can be of any of the cancers listed above. The T cell can be a CD8+ T cell or a CD4+ T cell. The compound can be a fusion protein, e.g., the fusion protein described above.

As used herein, "enhancing T cell responsiveness" means enhancing the ability of a T cell to respond to an immunogenic stimulus. The enhancement is not limited by any particular mechanism of action and can mean, for example, reversing (completely or partially) inhibition of the ability of the T cell to proliferate or by preventing the cell from dying by, for example, apoptosis or necrosis.

As used herein, "interferes with an interaction between the T cell and B7-H1" means:

(a) completely blocks a physical interaction between the T cell and B7-H1 such that there is substantially no physical interaction between the T cell and a B7-H1 molecule; or (b) modifies the physical interaction of the T cell with a B7-H1 molecule such that the physical interaction either does not deliver a signal to the T cell or delivers a signal to the T cell that does not substantially result in either death of the T cell or inhibition of the T cell's function, e.g., cytotoxic or helper activity.

As used herein, a "functional fragment" of a B7-H1 polypeptide is a fragment of the B7-H1 polypeptide that is shorter than the full-length polypeptide and has the ability to bind to a T cell. As used herein, a functional fragment of a receptor for B7-H1 (e.g., PD-1) is a fragment of the receptor for B7-H1 that has the ability to bind to B7-H1. Methods of establishing whether one polypeptide can bind to a cell or another polypeptide are known in the art.

As used herein, "inhibiting proliferation of a cancer cell" means either completely inhibiting proliferation of the cancer cell or substantially reducing the rate of proliferation of the cancer cell, e.g., reducing the rate of proliferation by 10%; 20%; 30%; 40%; 50%; 60%; 70%; 80%; 90%; 95%; 98%; 99%; or 99.5%; or 99.9%.

As used herein, the term "antibody" refers not only to whole antibody molecules, but also to antigen-binding fragments, e.g., Fab, F(ab')$_2$, Fv, and single chain Fv (sFv) fragments. An sFv fragment is a single polypeptide chain that includes both the heavy and light chain variable regions of the antibody from which the sFv is derived. Such fragments can be produced, for example, as described in U.S. Pat. No. 4,642,334, which is incorporated herein by reference in its entirety. Also included are chimeric antibodies. Chimeric antibodies are recombinant antibodies comprising portions derived from more than one species; for example, the antigen binding regions (i.e., the complementarity determining regions (CDR)), of the antibody molecule can be derived from a mouse wild-type antibody molecule and framework and constant regions can be derived from a human antibody molecule or human antibody molecules.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing T cell activity, will be apparent from the following description, from the drawings and from the claims.

DESCRIPTION OF DRAWINGS

FIG. 8A) and the percent of apoptotic IB2$^+$ cells (FIG. 8B) peritoneal cells recovered from P815 tumor-bearing RAG-1$^{-/-}$ immunodeficient mice at the indicated time points after i.p. injection with preactivated T cells (expressing the 2C transgenic TCR) ($2.5\times10^6$ per mouse) from mice transgenic for the TCR specific peptide expressed by P815 tumor cells. The preactivated T cells were prepared by culturing T cells purified from the spleens and lymph nodes of the 2C transgenic mice with irradiated spleen cells from BALB/c mice in the presence of human interleukin-2 (10 U/ml) for 3 days. The T cells were harvested from the cultures and depleted of dead cells by centrifugation over LYMPHOLYTE®-M lymphocyte separation medium prior to injection. The tumor cells ($1\times10^5$ per mouse) injected i.p. into the RAG-1$^{-/-}$ mice three days before injection of the preactivated T cells were P815 cells stably transfected with a either a control expression vector (Mock/P815) or an expression vector containing cDNA fragment encoding mB7-H1 (B7-H1/P815). The cells expressing the 2C transgenic receptor were detected by FFC after staining with a phycoerythrin-conjugated mAb (1B2) specific for the 2C TCR and apoptotic cells were detected by FFC after staining with FITC-labeled Annexin V.

DETAILED DESCRIPTION

Figure 1:
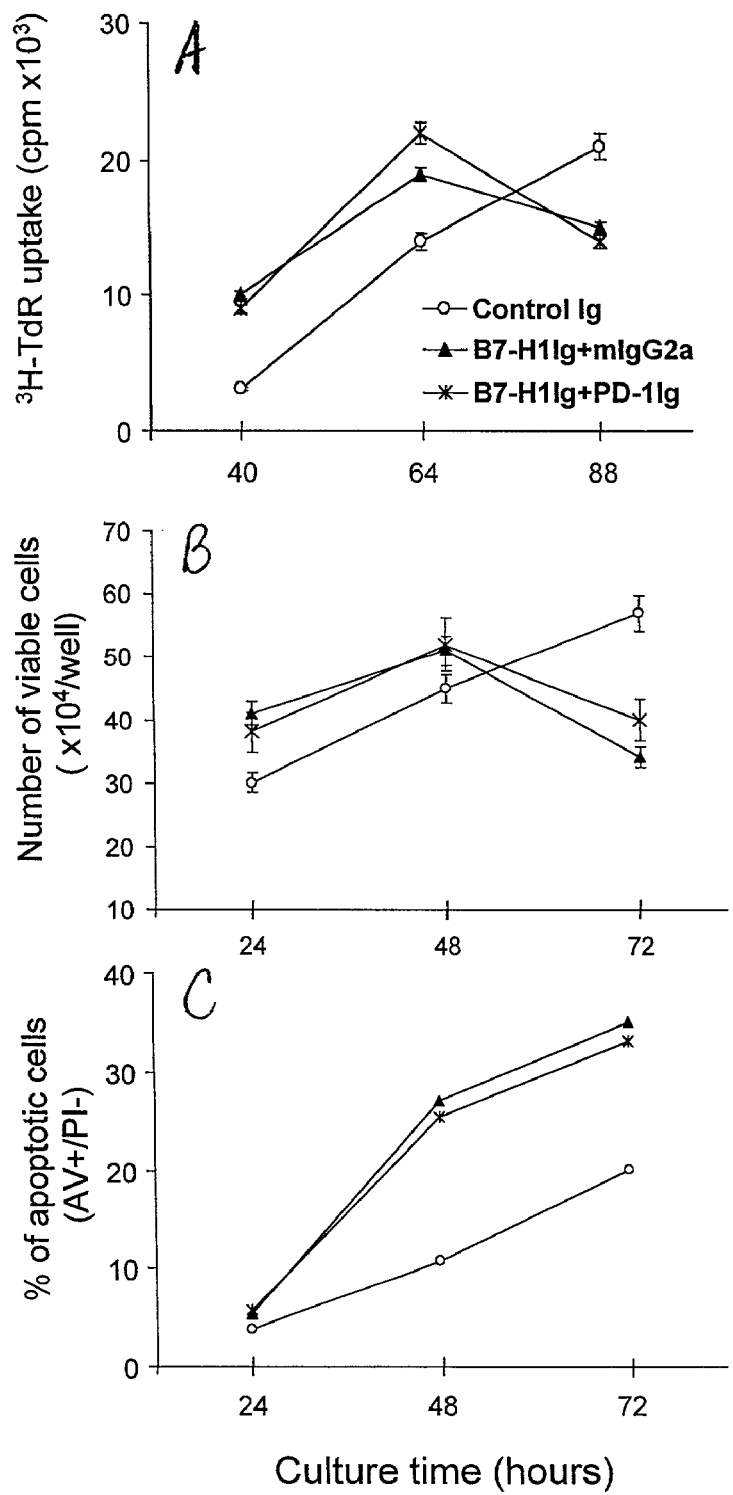
FIG. 1A is a line graph showing the level of T cell proliferation measured as counts per minute (cpm×10$^3$) of $^3$H-thymidine incorporated ($^3$H-TdR uptake) into T cells after 40, 64, and 88 hours of culture of purified human T cells (2×10$^5$ per well) in the presence of tissue culture plate-bound hB7-H1Ig fusion protein (or control Ig) (each coated onto the plates at a concentration of 10 μg/ml) and tissue culture-plate-bound antibody specific for human CD3 (coated onto the plates at a concentration of 500 ng/ml). Some culture wells contained soluble PD-1Ig fusion protein (or control mouse IgG2a (mIgG2a)) (each at a concentration of 30 μg/ml).
FIG. 1B is a line graph showing the concentration of viable cells (measured using the trypan blue exclusion assay) after 40, 64, and 88 hours of culture of purified human T cells (2×105 per well) in the presence of tissue culture-plate-bound hB7-H1Ig fusion protein (or control Ig) (each coated onto the plates at a concentration of 10 μg/ml) and tissue culture-plate-bound antibody specific for human CD3 (coated onto the plates at a concentration of 500 ng/ml). Some culture wells soluble PD-1Ig fusion protein (or control mouse IgG2a (mIgG2a)) (each at a concentration of 30 μg/ml).
FIG. 1C is a line graph showing the concentration of apoptotic cells (detected by fluorescence flow cytometry (FFC) as cells staining with Annexin V (AV+) and not staining with propidium iodide (PI−)) after 40, 64, and 88 hours of culture of purified human T cells (2×10$^5$ per well) in the presence of tissue culture-plate-bound hB7-H1Ig fusion protein (or control Ig) (each coated onto the plates at a concentration of 10 μg/ml) and tissue culture-plate-bound antibody specific for human CD3 (coated onto the plates at a concentration of 500 ng/ml). Some culture wells contained soluble PD-1Ig fusion protein (or control mouse IgG2a (mIgG2a)) (each at a concentration of 30 μg/ml).

The inventor discovered that, while B7-H1 enhanced the proliferation of T cells in response to suboptimal T cell receptor (TCR) activation in short term cultures, it inhibited the proliferation of the T cells in long-term cultures. In addition, in long-term cultures, B7-H1 enhanced apoptosis of the T cells.

The inventor also found that a wide variety of human tumor cells either constitutively express hB7-H1 on their surfaces or express it on their surfaces after exposure to interferon-γ (IFN-γ). While most normal tissues (e.g., breast, colon, pancreas, kidney, uterus, skeletal muscle, lung, liver, tonsil, and intestine) do not express hB7-H1, it was found on at least some macrophages.

The cells of a hB7-H1-expressing human mucoepidermoid lung carcinoma cell line, when cultured with peripheral blood T cells, caused enhanced apoptosis of the T cells, with the majority of apoptotic T cells being CD4+. This enhanced apoptosis was inhibited by a monoclonal antibody (mAb) specific for hB7-H1 and by a soluble fusion protein containing hB7-H1.

Cells of a human melanoma line (624mel) that do not constitutively express hB7-H1 were transfected with an expression vector so as to express cell surface hB7-H1. The resulting recombinant melanoma cells were found to enhance apoptosis of human T cells in a manner similar to the cells of the lung carcinoma line. Cells of a second human melanoma line (Skmel-28) treated with interferon γ (IFN-γ) were found to enhance the apoptosis of the cells of a CD4+ T cell clone specific for a melanoma peptide epitope and the enhanced apoptosis was inhibited by a mAb specific for hB7-H1.

The recombinant 624mel melanoma cells also induced apoptosis in a significantly higher number of cells of a CD8+ cytotoxic T cell (CTL) clone specific for a melanoma peptide epitope than did mock-transfected melanoma cells. This increased apoptosis was inhibited by both a mAb specific for hB7-H1 and by a fusion protein (PD-1Ig) containing the putative receptor (PD-1) for hB7-H1 and a part of the constant region of mouse IgG2a.

In addition, cells of a human breast cancer cell line that constitutively express hB7-H1 on their surfaces were found to induce apoptosis in cells of a CTL clone specific for a peptide epitope produced by the human breast cancer cells. Moreover, the apoptosis of these CTL was reduced by inclusion in the relevant of a mAb specific for B7-H1 in the culture medium.

Antibody inhibition experiments indicated that interleukin-10 (IL-10) and the Fas—Fas ligand (FasL) interaction are involved in B7-H1-induced apoptosis. Finally, experiments in an adoptive transfer model showed that mB7-H1 also enhances apoptosis of T cells in vivo.

These findings provide support for the methods of the invention, which are described below.

Methods of Enhancing the Activity of a T Cell

The methods of the invention involve enhancing the responsiveness of a T cell. These methods are based on the findings that the co-stimulatory B7-H1 molecule decreases proliferation and/or apoptosis of T cells and that agents that interfere with the physical interaction between B7-H1 a T cell reverse, completely or partially, this inhibitory effect. Thus the methods of the invention involve enhancing the responsiveness of T cells using compounds that contain agents that interfere with the physical interaction between B7-H1 and a T cell.

Since a wide variety of cancer cells express B7-H1 on their surfaces, the methods of the invention are particularly useful for enhancing T cell responsiveness where a physical interaction between a T cell and B7-H1 on a cancer cell can occur. Hence the methods of the invention can be applied to the treatment of cancer. Cancer cells can be breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, bladder cancer cells or any other cancer cells listed herein.

In in vivo methods of the invention, prior to administration of enhancing compound of the invention to subject with cancer, and in in vitro methods of the invention, prior to culturing an enhancing compound of the invention with a T cell and a cancer cell, the cells of the relevant cancer can optionally be tested for expression of B7-H1 by methods known in the art such as those disclosed herein. Cells can be tested for expression of a polypeptide by, for example, fluorescence flow cytometry, fluorescence microscopy, or immunohistochemistry. In addition, lysates of cells or culture supernatants of cells can be tested for the presence of the polypeptide of interest by electrophoretic methods optionally combined with immunoblotting methods. Moreover, immunoblotting can be performed without electrophoresis. Lysates and culture supernatants of cells can also be tested by methods such as ELISA. RNA in or isolated from the cells can also be analyzed for the presence of mRNA transcribed from the gene encoding the protein by, for example, in situ hybridization, spot blotting, Northern blotting, or reverse transcriptase-polymerase chain reaction (RT-PCR) analysis. In addition, body fluids (e.g. blood or urine) of a subject (e.g., a human cancer patient) can be tested by the above methods for the presence of higher than normal levels of B7-H1. Moreover, appropriately labeled (e.g., radiolabeled or fluorescently labeled) antibodies specific for B7-H1 can be used as agents to detect expression of B7-H1 by a cancer using established in vivo imaging (e.g., radiological) techniques.

However these methods are not limited to enhancing the responsiveness of a T cell whose responsiveness is inhibited by cancer cells. The methods of the invention can be applied to enhancing the responsiveness of a T cell that is exposed to any cell that expresses B7-H1 and for which the T cell, by virtue of the antigen specific T cell receptor (TCR) it expresses, has specific responsiveness. Such a cell can be, for example, an APC (e.g., a dendritic cell, a macrophage, a monocyte, or a B lymphocyte) that has a major histocompatibility complex (MHC) (class I or class II) molecule-peptide epitope molecular complex on its surface for which a relevant T cell is restricted and specific. Appropriate peptide epitopes include those derived from any of a variety of cancer cells (e.g., any of those listed herein) or infectious microorganisms (see below). Since cancer cell-derived peptide epitopes can be presented to T cells of interest by B7-H1-expressing APC, the methods of the invention can be applied to treatment of cancers other than those expressing cell-surface B7-H1.

Peptide epitopes can also be derived from any of a variety of infectious microorganisms. It is understood that relevant cells need not be classical APC but can be any B7-H 1-expressing cells (or cells in which B7-H1 expression is inducible by, for example, IFN-γ) infected with an appropriate infectious microorganism. Such cells include, without limitation, T cells, tissue epithelial cells, endothelial cells, and fibroblasts. Thus, the methods of the invention can be applied to the treatment of infections by any of a wide variety of infectious microorganisms. While such microorganisms will generally be those that replicate inside a cell (commonly designated intracellular pathogens), since APC presenting peptide epitopes derived from infectious microorganism that are not necessarily in the relevant APC, the methods of the invention can also be applied to situations involving infectious microorganisms that replicate extracellularly or in cells that do not express B7-H1. Relevant microorganisms can be viruses, bacteria, mycoplasma, fungi (including yeasts), and protozoan parasites and specific examples of such microorganisms include, without limitation, *Mycobacteria tuberculosis, Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gingivalis*, mycoplasma, *Histoplasma capsulatum, Cryptococcus neoformans, Chlamydia trachomatis, Candida albicans, Plasmodium falciparum, Entamoeba histolytica, Toxoplasma brucei, Toxoplasma gondii, Leishmania major* human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus.

Compounds that can be used to enhance the responsiveness of a T cell (e.g., a CD4+ T cell or a CD8+ T cell) can be, or contain agents, that interfere with the interaction between a T cell and B7-H1 or functional fragments of such agents. These compounds are referred to herein as "enhancing compounds." Appropriate agents include antibodies that bind to B7-H1, cell-free, soluble forms of receptors for B7-H1 (e.g., PD1), or cell-free, soluble forms of B7-H1.

Such agents or functional fragments can have amino acid sequences identical to wild-type sequences or they can contain no more than 100 (e.g., no more than: two; three; four; five; six; seven; eight; nine; 10; 12; 14; 17; 20; 25; 30; 35; 40; 50; 60; 70; 80; 90; or 100) conservative amino acid substitutions.

The enhancing compounds can be administered to subjects or added to cultures alone or together with any of a variety of immunogenic stimuli. As used herein, an "immunogenic stimulus" is a stimulus delivered to a T cell via the antigen-specific T cell receptor (TCR) expressed on the surface of the T cell. More commonly, but not necessarily, such a stimulus is provided in the form of an antigen for which the TCR is specific. While such antigens will generally be protein, they can also be carbohydrates, lipids, nucleic acids or hybrid molecules having components of two or more of these molecule types, e.g., glycoproteins or lipoproteins. However, the immunogenic stimulus can also be provided by other agonistic TCR ligands such as antibodies specific for TCR components (e.g., TCR α-chain or β-chain variable regions) or antibodies specific for the TCR-associated CD3 complex. Immunogenic stimuli (as used herein) do not include antigen-non-specific stimuli provided by non-specifically acting factors such as, for example, cytokines (e.g., e.g., interleukin-(IL-)1, IL-2, IL-3, IL-4, IL-5, IL-6, IL-10, IL-12, IL-13, IL-15, an interferon (IFN; e.g., IFN-α, IFN-β, IFN-γ), granulocyte colony-stimulating factor (G-CSF), granulocyte-macrophage colony stimulating factor (GM-CSF) or tumor necrosis factor-α (TNF-α)), co-stimulatory molecules, or adhesion molecules. Nevertheless such non-specifically acting factors can also be administered to appropriate subject or included in the T cell cultures described below.

Antigens useful as immunogenic stimuli include alloantigens (e.g., a MHC alloantigen) on, for example, an antigen presenting cell (APC) (e.g., a dendritic cell (DC), a macrophage, a monocyte, or a B cell). DC of interest are interdigitating DC and not follicular DC; follicular DC present antigen to B cells. For convenience, interdigitating DC are referred to herein as DC. Methods of isolating DC from tissues such as blood, bone marrow, spleen, or lymph node are known in the art, as are methods of generating them in vitro from precursor cells in such tissues. Also useful as immunogenic stimuli are polypeptide antigens and peptide-epitopes derived from them (see below). Unprocessed polypeptides are processed by APC into peptide-epitopes that are presented to responsive T cells in the form of molecular complexes with MHC molecules on the surface of the APC. Useful immunogenic stimuli also include a source of antigen such as a lysate of either tumor cells or cells infected with an infectious microorganism of interest. APC (e.g., DC) pre-exposed (e.g., by coculturing) to antigenic polypeptides, peptide-epitopes of such polypeptides or lysates of tumor (or infected cells) can also be used as immunogenic stimuli. Such APC can also be "primed" with antigen by culture with a cancer cell or infected cell of interest; the cancer or infected cells can optionally be irradiated or heated (e.g., boiled) prior to the priming culture. In addition, APC (especially DC) can be "primed" with either total RNA, mRNA, or isolated TAA-encoding RNA.

Alternatively, antigen as an immunogenic stimulus be provided in the form of cells (e.g., tumor cells or infected cells producing the antigen of interest). In addition, immunogenic stimuli can be provided in the form of cell hybrids formed by fusing APC (e.g., DC) with tumor cells [Gong et al. (2000) Proc. Natl. Acad. Sci. USA 97(6):2716-2718; Gong et al. (1997) Nature Medicine 3(5):558-561; Gong et al. (2000) J. Immunol. 165(3):1705-1711] or infected cells of interest. Methods of fusing cells (e.g., by polyethylene glycol, viral fusogenic membrane glycoproteins, or electrofusion) are known in the art. In discussing these cell hybrids, the tumor or infected cell partners will be referred to as the immunogenic cells (IC). Cells or cell hybrids can be used (as immunogenic stimuli) untreated or they can be metabolically inhibited (e.g., by irradiation or exposure to a drug such as mitomycin-C) so as to substantially ablate their ability to divide. Tumor or infected cells used per se as an immunogenic stimulus or as IC for the production of cell hybrids will preferably, but not necessarily, be derived from the same donor as that of the T cell. Where the cells are from a different donor, they will preferably share one MHC haplotype with the T cell. APC used to form cell hybrids will also preferably, but not necessarily, be derived from the same donor as the T cell. In the production of cell hybrids, either the APC or the IC will be preferably be from, or MHC-compatible with, the donor of the T cell. Alternatively, the APC and/or the IC can share one MHC haplotype (i.e., be semi-allogeneic) with the donor of the T cell. However, as the cells or hybrids used as immunogenic stimuli will frequently be used in the presence of APC of the T cell donor (e.g., in in vivo applications), they can be fully MHC incompatible with the T cell.

Also useful as immunogenic stimuli are heat shock proteins bound to antigenic peptide-epitopes derived from antigens (e.g., tumor-associated antigens or antigens produced by infectious microorganisms) [Srivastava (2000) Nature Immunology 1(5):363-366]. Such complexes of heat shock protein and antigenic peptide are useful for facilitating or enhancing uptake of antigenic peptides by APC. Heat shock proteins of interest include, without limitation, glycoprotein 96 (gp96), heat shock protein (hsp) 90, hsp70, hsp110, glucose-regulated protein 170 (grp170) and calreticulin. Immunogenic stimuli can include one or more (e.g., one, two, three, four, five, six, seven, eight, nine, ten, more) heat shock proteins isolated from tumor cells or infected cells. Such tumor or infected cells are preferably, but not necessarily, from the same subject (i) whose T cell responsiveness is to be enhanced by a method of the invention or (ii) from whom T cells (whose responsiveness is to be enhanced by a method of the invention) were obtained. The tumor or infected cells can also be obtained, for example, from another individual having the same or a related tumor-type or infection as the subject. Alternatively, the heat shock protein can be isolated from mammalian cells expressing a transcriptosome prepared from tumor cells or infected cells of interest.

Immunogenic molecules can be derived from a wide range of infectious microorganisms. Examples of relevant microorganisms include any of those listed above. Relevant microbial proteins include, without limitation, the B subunit of heat labile enterotoxin of *E. coli* [Konieczny et al. (2000) FEMS Immunol. Med. Microbiol. 27(4):321-332], heat-shock proteins, e.g., the *Y. enterocolitica* heat shock protein 60 [Konieczny et al. (2000) supra; Mertz et al. (2000) J. Immunol. 164(3):1529-1537] and M. tuberculosis heat-shock proteins hsp60 and hsp70, the *Chlamydia trachomatis* outer membrane protein [Ortiz et al. (2000) Infect. Immun. 68(3):1719-1723], the *B. burgdorferi* outer surface protein [Chen et al. (1999) Arthritis Rheum. 42(9):1813-1823], the *L. major* GP63 [White et al. (1999) Vaccine 17(17):2150-2161 (and published erratum in Vaccine 17(20-21):2755)], the *N. meningitidis* meningococcal serotype 15 PorB protein [Delvig et al. (1997) Clin. Immunol. Immunopathol. 85(2);134-142], the *P. gingivalis* 381 fimbrial protein [Ogawa, (1994) J. Med. Microbiol. 41(5):349-358], the *E. coli* outer membrane protein F [Williams et al. (2000) Infect. Immun. 68(5):2535-2545], influenza virus hemagglutinins and neuramindases, retroviral (e.g., HIV) surface glycoproteins (e.g., HIV gp160/120), or retroviral tat or gag proteins. CTL are by virtue of their ability to kill target cells infected with any of a wide variety of intracellular pathogens (e.g., viruses, or intracellular bacteria and protozoans) potent mediators of immunity to such pathogens. Thus, since the methods of the invention are efficient at enhancing CTL responses, they can be used for prophylaxis and/or or therapy in infections with such intracellular pathogens. In addition, helper T cells release a wide variety of cytokines that mediate pathogen-destructive inflammatory reponses.

As indicated above, immunogenic stimuli useful in the invention can be any of a wide variety of tumor cells, APC "primed" with tumor cells, hybrid cells (see above), tumor-associated antigens (TAA), peptide-epitopes of such TAA, and APC "primed" with TAA or peptide-epitopes of them. As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a TAA can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Examples of relevant tumors that can be used per se or as a source of antigen (see above) include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, renal cell cancer, pancreatic cancer, genitourinary tumors such ovarian cancer, vaginal cancer, bladder cancer, testicular cancer, prostate cancer or penile cancer, bone tumors, and vascular tumors. Relevant TAA include, without limitation, carcinoembryonic antigen (CEA), prostate specific antigen (PSA), MAGE (melanoma antigen) 1-4, 6 and 12, MUC (mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bc1-2, and Ki-67. Both CTL and helper T cells have been shown to be efficient effectors of tumor immunity.

Also useful for the invention are fusion proteins containing, as one domain, all or a portion of any of the polypeptide enhancing compounds (e.g., B7-H1), immunogenic stimuli, or non-specifically acting factors (e.g. cytokines) listed above. Additional domains in such fusion proteins can be additional functional domains or signal peptides. Such fusion proteins can also contain immunoglobulin heavy chain constant regions (e.g., mouse IgG2a or human IgG1 heavy chain constant regions) or portions of such constant regions (e.g., CH2 and/or CH3 domains). Useful additional domains include those that facilitate purification of the peptide, e.g., a hexahistidine sequence.

Polypeptide enhancing compounds, immunogenic stimuli, and non-specifically acting factors useful for the invention include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of polypeptides of interest. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to activate an immune response (in the case of immunogenic stimuli) and enhance an immune response (in the case of the enhancing compounds). Peptidomimetic compounds can have additional characteristics that enhance their in vivo utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Molecules useful as enhancing compounds, immunogenic stimuli, and non-specifically acting factors can be produced by any of a wide range of methods known in the art. They can be purified from natural sources (e.g., from any of the cancer cells or infectious microorganisms listed herein). Smaller peptides (fewer than 100 amino acids long) and other non-protein molecules can be conveniently synthesized by standard chemical means known to those in the art. In addition, both polypeptides and peptides can be manufactured by standard in vitro recombinant DNA techniques and in vivo transgenesis using nucleotide sequences encoding the appropriate polypeptides or peptides (see Nucleic Acids section below). Methods well-known to those skilled in the art can be used to construct expression vectors containing relevant coding sequences and appropriate transcriptional/translational regulatory elements. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

The transcriptional/translational regulatory elements referred to above include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing nucleic acid molecules encoding enhancing agents or immunogenic stimuli; yeast (for example, Saccharomyces and Pichia)

transformed with recombinant yeast expression vectors containing a nucleic acid encoding enhancing agents or immunogenic stimuli; insect cell systems infected with recombinant virus expression vectors (for example, baculovirus) containing a nucleic acid encoding enhancing agents or immunogenic stimuli; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a nucleotide sequence encoding; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors of the invention can then be used, for example, for large or small scale in vitro manufacture of enhancing agents or immunogenic stimuli by methods known in the art. In essence, such methods involve culturing the cells under conditions that maximize production of the polypeptide and isolating the polypeptide from the culture, i.e., the cells and/or the culture medium.

Methods of making antibodies are known in the art. For example, they can be produced by immunizing animals with a substance of interest (e.g., B7-H1). A useful antibody can be a polyclonal antibody present in the serum or plasma of an animal (e.g., human, non-human primate, mouse, rabbit, rat, guinea pig, sheep, horse, goat, cow, pig, or bird) which has been injected with the substance of interest, and optionally an adjuvant. Polyclonal antibodies can be isolated from serum or plasma by methods known in the art.

Monoclonal antibodies (mAb) can also be produced. Methods of making and screening monoclonal antibodies are well known in the art. Once the desired antibody-producing hybridoma has been selected and cloned, the resultant antibody can be produced by a number of methods known in the art. For example, the hybridoma can be cultured in vitro in a suitable medium for a suitable length of time, followed by the recovery of the desired antibody from the supernatant. The length of time and medium are known or can be readily determined.

Polyclonal and monoclonal antibodies can be manufactured in large amounts by methods known in the art. Thus, in the case of polyclonal antibodies, large animals (e.g., sheep, pigs, goats, horses, or cows) or a large number of small animals can be immunized as described above. Serum can be isolated from the blood of animals producing an antibody with the appropriate activity. If desired, polyclonal antibodies can be purified from such sera by methods known in the art. Monoclonal antibodies can also be produced in large amounts in vitro using, for example, bioreactors or in vivo by injecting appropriate animals with the relevant hybridoma cells. For example, mice or rats can be injected intraperitoneally (i.p.) with the hybridoma cells and, after a time sufficient to allow substantial growth of the hybridoma cells and secretion of the monoclonal antibody into the blood of the animals, they can be bled and the blood used as a source of the monoclonal antibody. If the animals are injected i.p. with an inflammatory substance such as pristane and the hybridoma cells, peritoneal exudates containing the monoclonal antibodies can develop in the animals. The peritoneal exudates can then be "tapped" from the animals and used as a source of the appropriate monoclonal antibody.

For the methods of the invention, it is often required that the enhancing compounds, immunogenic stimuli, and non-specifically acting factors be purified. Methods for purifying biological macromolecules (e.g., proteins) are known in the art. The degree of purity of the macromolecules can be measured by any appropriate method, e.g., column chromatography, polyacrylamide gel electrophoresis, or HPLC analysis.

The methods of the invention can be performed in vitro, in vivo, or ex vivo. In vitro application of the methods can be useful, for example, in basic scientific studies of apoptosis. They can also be useful as assays for T cell responsiveness to a tumor-specific or infectious microorganism-derived antigen where T cell proliferation can be low and possibly undetectable in the absence of a compounds that contain agents that interfere with the physical interaction between a B7-H1 and a T cell. Thus, the methods of the invention can be used as diagnostic assays for cancers and infectious disease. The methods can also be useful for growing up large numbers of T cells (e.g., tumor infiltrating lymphocytes (TIL)) for adoptive immunotherapy of cancer or infectious diseases.

In the in vitro methods of the invention, lymphoid cells (consisting of or including T cells) obtained from a mammalian subject are cultured with any of the above described enhancing compounds and immunogenic stimuli. The lymphoid cells can be from a subject pre-exposed to a relevant antigen (in any of the forms described above); alternatively, the donor of the lymphoid cells need not have been exposed to the antigen. The cultures can also be supplemented with one or more cytokines or growth factors listed herein. The cultures can also be monitored at various times to ascertain whether the desired level of immune reactivity (e.g., CTL or helper T cell activity) has been attained.

The methods of the invention will preferably be in vivo or ex vivo (see below). The methods are generally useful in enhancing T cell responsiveness in subjects with cancer and infectious diseases. The enhancement of T cell responsiveness effected by the methods of the invention can result in decreased cancer cell or infectious microorganism proliferation. The methods of the invention can be applied to mammalian subjects (e.g., human breast cancer or melanoma patients) alone or in conjunction with other drugs and/or radiotherapy.

The methods of the invention can be applied to a wide range of species, e.g., humans, non-human primates (e.g., monkeys or chimpanzees), horses, cattle, pigs, sheep, goats, dogs, cats, rabbits, guinea pigs, hamsters, rats, and mice.

In Vivo Approaches

In that methods of invention enhance T cell responsiveness, they are generally useful for enhancing immune responses. Such immune responses can be prophylactic or therapeutic. However, the responses enhanced need have neither prophylactic nor therapeutic efficacy. They can be used, for example, (a) to produce large numbers of activated T cells for use in basic scientific studies of T cell activity; or (b) to enhance T cell responses that provide helper activity for antibody-producing B cells and thereby facilitate the production of large quantities of antibodies in mammals (e.g., rabbits, goats, sheep, or horses) that are subsequently isolated from the animals and used for purposes such as antigen detection or purification, or (c) for immunization of animals (e.g., mice, rats, or hamsters) with a view to making monoclonal antibodies.

The methods of the invention can be used, for example, for prophylaxis or therapy against (a) infectious diseases due to any of the infectious agents listed herein; or (b) cancers such as any of those listed herein. In addition to being useful for the treatment of a wide variety of diseases, in cases where a subject is at relatively high risk for a cancer (e.g., prostate cancer in men over 50 years of age, lung cancer in a tobacco smoker, or melanoma in a subject with multiple nevi), appropriate methods can be used for prophylaxis. In regard to infectious microorganisms, the methods can be particularly useful in the prevention and/or therapy of diseases involving intracellular microorganisms (i.e. infectious agents that replicate inside a cell), e.g., viruses such as influenza virus or HIV, intracellular bacteria such *M. tuberculosis*, and intracellular protozoans such as *P. falciparum* or any of the other infectious agents listed herein.

As used herein, "prophylaxis" can mean complete prevention of the symptoms of a disease, a delay in onset of the symptoms of a disease, or a lessening in the severity of subsequently developed disease symptoms. "Prevention" should mean that symptoms of the disease (e.g., an infection) are essentially absent. As used herein, "therapy" can mean a complete abolishment of the symptoms of a disease or a decrease in the severity of the symptoms of the disease. As used herein, a "protective" immune response is an immune response that is prophylactic and/or therapeutic.

In one in vivo approach, the enhancing compound itself, and optionally an immunogenic stimulus and/or one or more nonspecifically acting factors (see above), is administered to the subject. Generally, the substances to be administered will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They are preferably delivered directly to a site of infection or tumor cells, e.g., to a tumor or a tumor bed following surgical excision of the tumor, in order to kill any remaining tumor cells. Alternatively, they can be delivered to lymphoid tissue (e.g., lymph nodes or spleen) draining the site of infection or tumor. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-1,000.0 µg/kg. Wide variations in the needed dosage are to be expected in view of the variety of enhancing compounds available and the differing efficiencies of various routes of administration. For example, oral administration would be expected to require higher dosages than administration by intravenous. injection. Variations in these dosage levels can be adjusted using standard empirical routines for optimization as is well understood in the art. Administrations can be single or multiple (e.g., 2-, 3-, 4-, 6-, 8-, 10-, 20-, 50-,100-, 150-, or more fold). Encapsulation of the substances in a suitable delivery vehicle (e.g., polymeric microparticles or implantable devices) may increase the efficiency of delivery, particularly for oral delivery. Immunogenic stimuli, and/or non-specifically acting factors can be administered before at the same time as, or after administration of the enhancing compounds.

In addition, where immunogenic stimuli are administered, adjuvants can be used together with the immunogenic stimuli. Suitable adjuvants include cholera toxin (CT), *E. coli* heat labile toxin (LT), mutant CT (MCT) [Yamamoto et al. (1997) J. Exp. Med. 185:1203-1210] and mutant *E. coli* heat labile toxin (MLT) [Di Tommaso et al. (1996) Infect. Immunity 64:974-979]. MCT and MLT contain point mutations that substantially diminish toxicity without substantially compromising adjuvant activity relative to that of the parent molecules. Other useful adjuvants include alum, Freund's complete and incomplete adjuvant, and RIBI. In addition, one or more of the above-listed cytokines or growth factors can be administered (by any of the routes recited herein) to the subject, before, at the same time as, or after administration of the enhancing agents and, optionally, immunogenic stimuli. Moreover, where tumor cells, APC, or hybrid cells are used as the immunogenic stimulus, such cells, can express on their surface or secrete either (a) one or more recombinant costimulatory molecules (e.g., B7.1, B7.2, B7-H2, B7-H3, or B7-H4) and/or (b) one or more recombinant cytokines or recombinant growth factors such as those listed above, e.g., GM-CSF. Cells expressing on their surface or secreting the above recombinant molecules will have been transfected (stably or transiently) or transformed with one or more nucleic acids (e.g., expression vectors) encoding the molecules.

Alternatively, a polynucleotide containing a nucleic acid sequence encoding a polypeptide enhancing compound can be delivered to cancer cells or a site of infection in a mammal. Expression of the coding sequence will preferably be directed to lymphoid tissue of the subject by, for example, delivery of the polynucleotide to the lymphoid tissue. Expression of the coding sequence can be directed to any cell in the body of the subject. However, expression will preferably be directed to cells in the vicinity of the tumor cells whose responsiveness it is desired to inhibit. In certain embodiments, expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73, 479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the enhancing compound polypeptide of interest with an initiator methionine and optionally a targeting sequence is operatively linked to a promoter or enhancer-promoter combination.

Short amino acid sequences can act as signals to direct proteins to specific intracellular compartments. Such signal sequences are described in detail in U.S. Pat. No. 5,827,516, incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Ex Vivo Approaches

Lymphoid cells (e.g., peripheral blood mononuclear cells (PBMC)) can be obtained from a subject (e.g., a human cancer patient), or another suitable donor, and exposed in tissue culture to an enhancing compound and optionally, any other of immunogenic stimuli listed herein. The cultures can also contain any of a variety of cytokines (see above) The lymphoid cells containing highly activated T cells are then introduced into the same or a different patient.

Another ex vivo strategy can involve transfecting or transducing cells obtained from the subject with a polynucleotide encoding an enhancing compound. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the enhancing compound for as long as they survive in the subject. Alternatively, tumor cells, preferably obtained from the subject but potentially from an individual other than the subject, can be transfected or transformed by a vector encoding an enhancing compound. The tumor cells, preferably treated with an agent (e.g., ionizing irradiation) that ablates their proliferative capacity, are then introduced into the patient, where they secrete the enhancing compound.

These ex vivo methods include the steps of harvesting cells from a subject, culturing the cells, transducing them with an expression vector, and maintaining the cells under conditions suitable for expression of the enhancing compound. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the subject.

It is understood that the methods of invention can involve combinations of the above in vivo and ex vivo approaches. Thus, for example, an immunogenic stimulus can be provided in the form of a peptide-epitope and the enhancing compound in the form of either a nucleic acid encoding it or cells transformed with a nucleic acid encoding it.

The methods of the invention can be applied to any of the diseases and species listed here. Methods to test whether a given modality is therapeutic for or prophylactic against a particular disease are known in the art. Where a therapeutic effect is being tested, a test population displaying symptoms of the disease (e.g., cancer patients) is treated by a method of the invention, using any of the above described strategies. A control population, also displaying symptoms of the disease, is treated, using the same methodology, with a placebo. Disappearance or a decrease of the disease symptoms in the test subjects would indicate that the method was therapeutic.

By applying the same strategies to subjects prior to onset of disease symptoms (e.g., presymptomatic subjects considered to likely candidates for cancer development (see above)) or experimental animals in which an appropriate disease spontaneously arises or can be deliberately induced, e.g., multiple murine cancers, the method can be tested for prophylactic efficacy. In this situation, prevention of onset of disease symptoms is tested. Analogous strategies can be used to test for the efficacy of the methods in the prophylaxis of a wide variety of infectious diseases, e.g., those involving any of the microorganisms listed above.

The following examples serve to illustrate the invention and not to limit it.

EXAMPLES

Example 1

Materials and Methods

Monoclonal Antibodies Fusion Proteins and Fluoresence Flow Cytometry (FFC) Analysis Female BALB/c mice (National Cancer Institute, Frederick, Md.) were immunized with a purified fusion protein consisting of the human B7-H1 polypeptide fused to CH2-CH3 domains of the constant region of the heavy chain of mouse IgG2a (hB7-H1Ig) [Dong et al. (1999) Nature Med. 5:1365-1369]. Splenocytes from mice with high antibody titers were fused with SP2/0 cells to produce hybridomas. Several rounds of selection by ELISA and FFC yielded 4 clones (2H1, 5H1, 7H1 and 8H1) producing mAb that specifically stained hB7-H1-transfected 293 cells. mAbs were purified from hybridoma culture supernatants by adsorption to and elution from Protein G-SEPHAROSE™ (Pierce, Rockford, Ill.) immunoglobulin G affinity chromatography matrix, and were dialyzed in LPS-free PBS. Clones 2H1 and 5H1 were used for the studies described in the following examples. Both mAbs are IgG1 and have similar staining patterns and blocking activity. The PD-1Ig fusion protein was prepared as described [Chapoval et al. (2000) Methods Mol. Med. 45:247-255]. F(ab')$_2$ fragments of anti-hB7-H1 mAb (5H1) were prepared by digestion and purification using an Immobilized Pepsin Kit (Pierce, Rockford, Ill.). Anti-2C mAb specific for the T cell receptor (TCR) expressed on T cells of 2C TCR transgenic mice was purified from culture supernatants of hybridoma 1B2 [Sykulev et al. (1994) Proc. Natl. Acad. Sci. USA 91:11487-11491] and conjugated with phycoerythrin (PE). The mAbs specific for CD8 (RPA-T8), Fas (DX2) and Fas ligand (NOK-1) were purchased from BD PharMingen (San Diego, Calif.) and the rabbit anti-human TRAIL polyclonal antibody was purchased from Alexis Biochemicals (San Diego, Calif.). The phenotypes of T cells and tumor cells were analyzed by staining with specific mAb and fluorescence was analyzed by FFC using a FACSCAN™ (Becton Dickinson, Mountain View, Calif.) fluorescence-activated cell sorter and CELLQUEST™ software (Becton Dickinson, San Jose, Calif.).

Histology and Immunohistochemical Analysis

Human tumor cell lines were either purchased from ATCC or established in the inventors' laboratories at the Mayo Clinic [Kobayashi et al. (2000) Cancer Res. 60:5228-5236; Yu et al. (2001) Ann. Neurol. 49:146-154]. Cells were stained by incubation with anti-hB7-H1 mAb (2 μg/sample) at 4° C. After 30 min, the cells were washed and further incubated with FITC- or PE-conjugated (Biosource, Camarillo, Calif.) F(ab')$_2$ goat anti-mouse IgG for 30 min at 4° C. Human cancer or normal tissue samples were obtained from Mayo Clinic's Department of Pathology with Internal Review Board approval. Frozen tissues were sectioned and stained with anti-hB7-H1 mAb (5H1) or control antibody (mIgG1) using a standard immunohistochemical protocol in the Pathology Core Facility of the Mayo Clinic Cancer Center.

Transfection

Human melanoma 624mel cells were transfected with the pcDNA3 plasmid containing a full length hB7-H1 coding sequence [Dong et al. (1999) Nature Med. 5:1365-1369] and transfectants were selected by G418 resistance. A high expressing clone (B7-H1/624mel) was sorted by fluorescence-activated cell sorting (FACS) using 5H1 mAb. The Mock/624mel control line was generated by transfection of wild type 624mel cells with the pcDNA3 plasmid without an expressible insert. Mock/P815 and B7-H1/P815 were described previously [Tamura et al. (2001) Blood 97:1809-1816]. All cell lines were maintained in a complete tissue culture medium of RPMI-1640 (Life Technologies, Rockville, Md.) supplemented with 10% fetal bovine serum (FBS; HyClone, Logan, Utah), 25 mM HEPES, 100 U/ml penicillin G and 100 μg/ml streptomycin sulfate.

Human T Cells

To obtain purified human CD4+ T cells, PBMC were isolated by nylon wool (80% purity) or ROSETTESEP® Human T cell enrichment cocktail (>95% purity) (Stemcell, Canada). The assay for costimulatory function of hB7-H1Ig protein has been described [Dong et al. (1999) Nat. Med. Vol. 5: 1365-1369; and copending U.S. application serial nos. 09/451,291 and 09/649,108]. T cell proliferation was determined after adding 1.0 mCi $^3$H-thymidine ($^3$H-TdR) at least 18 hrs before cell harvest. Incorporation of $^3$H-TdR was measured with a MICROBETA® TriLux liquid scintillation counter (Wallac, Finland). Cell viability was analyzed by trypan blue exclusion. To block the effects of immobilized hB7-H1Ig, 20-30 μg/ml of soluble human PD-1Ig or control Ig (mouse IgG2a) was added 30 min before adding CD4+ T cells.

Tumor-specific CD4+ and CD8+ T cell clones were generated by in vitro stimulation with dendritic cells loaded with corresponding tumour antigens or peptide epitopes [Kobayashi et al. (2000) Cancer Res. Vol. 60: 5228-5236; Lu et al. (2000) Cancer Res. Vol. 60: 5223-5227].

Generation of Antigen-Specific Cytotoxic T Cells (CTL)

Tumor antigen-specific CD8+ human T cell clones were generated by in vitro stimulation with dendritic cells loaded with corresponding peptide epitopes as described previously [Lu et al. (2000) Cancer Res. 60:5223-5227]. M15 is a human CD8+ CTL clone that specifically recognizes an HLA-A2-restricted epitope (IMDQVPFSV) (SEQ ID NO: 1) of the gp100 melanoma antigen. M99 is an HLA-B7-restricted CD8+ CTL clone [Lu et al. (2000) Cancer Res. 60:5223-5227] that recognizes an epitope (IPQQHTQVL) (SEQ ID NO: 2) of carcinoembryonic antigen. A standard 4-hour $^{51}$Cr release cytotoxicity assay was performed to assay CTL activity.

To activate 2C T cells, 4×10$^7$ CD8$^+$ T cells were purified from spleen and lymph nodes of 2C mice by MACS® magnetic cell separation beads (Miltenyi Biotec, Miltenyi, Germany) and subsequently stimulated with irradiated BALB/c spleen cells in the presence of 10 U/ml human IL-2. Three days later, T cells were harvested, depleted of dead cells by centrifugation over Lympholyte-M (Cedarlane Laboratories, Hornby, Ontario, Canada), and used for adoptive transfer.

Cell Apoptosis Assays

The human CD4+ T cell clones 4D16 and 8G9, and CD8+ T cell line (M15) were cultured for 2 weeks as described previously [Kobayashi et al. (2000) Cancer Res. 60:5228-5236] with γ-irradiated allogeneic PBMC and EBV-transformed B cells in RPMI 1640 medium containing 15% FBS and interleukin-2 (50 U/ml). To assay apoptosis of CD4+ T cell clones, the human melanoma cell line SKmel-28 was incubated with medium alone or 2000 IU/ml of IFN-γ for 48 hr to induce the expression of MHC class II and hB7-H1 and then irradiated by $^{60}$Co at 14K Rad. For activation of syngeneic CD4+ T cells, IFN-γ treated SKmel-28 were pulsed with 10 mg/ml of MAGE-3 p146-160 peptide for 2 h at 37° C. After washing, SKmel-28 cells were incubated with the control mIgG1 or anti-B7-H1 mAb (2H1) for 30 min at 37° C. before co-culture with T cells. Pre-activated CD4+ T cells at 2×105 cells/well were co-cultured at 37° C. for 6 days with tumor cells at 2×104 cells/well (T cell to tumor cell ratio of 10:1) in the presence of blocking agents or control mouse IgG1.

For evaluation of apoptosis of human CD8+ T cell clones, the CTL (M15 or M99 clones) (2×10$^5$ cells/well) were cultured with irradiated tumor cells (1-5×10$^4$ cells/well) for 4-5 days. Monoclonal antibodies, fusion protein and control IgG were included in the culture ab initio. Cells were harvested at the indicated times and stained with Annexin V and anti-CD8 mAb. The cells were analyzed by a FACScan and apoptosis was calculated as the percentage of Annexin V-staining cells gated in the CD8-expressing populations.

For in vivo assays of 2C T cell apoptosis, female RAG-1$^{-/-}$ mice in groups of 3 were inoculated i.p. with 1×10$^5$ mock/P815 or B7-H1/P815 cells. Three days later, preactivated 2C TCR transgenic T cells (2.5×10$^6$) were injected i.p. into each tumor-bearing mouse. Peritoneal cells were collected, counted at each time point as indicated, and stained with PE-conjugated 1B2 mAb and FITC-labeled Annexin V. Apoptosis was calculated as the percentage of Annexin V-staining cells gated in the 1B2-expressing population. Data are presented as means ±SD of data from 3 mice for each point in more than three experiments.

For assay of apoptotic T cells after exposure of polyclonal T cells to tumor cells, human peripheral blood T cells (2×105 cells/well) were cultured with irradiated NCI-H292 cells (4×104 cells/well) for 5 days. Blocking agents such as anti-hB7-H1 mAb (2H1), hB7-H1Ig, PD-1Ig fusion proteins or mouse IgG1 (as control) were added (20 mg/ml) at the beginning of cell co-culture. Harvested cells were stained with 7-AAD, anti-CD4 and anti-CD8 mAbs. Both early and late apoptotic cells were gated as R2 and viable cells as R3. The cells in the R2 and R3 gates were analyzed for expression of CD4 or CD8.

In another assay for apoptosis of polyclonal T cells, human peripheral blood T cells were isolated and purified by ROSETTESEP® Human T cell enrichment cocktail (Stemcell, Canada) to obtain purified T cells (>95%). T cells at a concentration of 2×10$^5$/well (3 wells per group) were cultured in 96-well flat-bottomed tissue culture plates that had been pre-coated overnight with 0.5 μg/ml of anti-CD3 mAb (clone HIT3a, PharMingen, Palo Alto, Calif.) in the presence of immobilized hB7-H1Ig or control Ig (mouse IgG2a) for 72 hours. Both the hB7-H1Ig and control Ig were pre-coated onto the plates at a concentration of 10 μg/ml. Aliquots (1 × $10^5$) of T cells were stained with FITC-conjugated Annexin V (PharMingen) (5 μl /test) and propidium iodide (PI) (Sigma) (5 μg/ml) for 1 hr, and the samples were analyzed by FFC. Apoptosis was calculated as the percentage of Annexin V-staining cells in the viable cell fraction. For blocking of apoptosis induced by stimulation with anti-CD3 mAb and hB7-H1Ig, human PD-1Ig (30 μg/ml), a neutralizing mAb specific for human IL-10 (5 μg/ml; JES3-9D7; PharMingen), or a neutralizing mAb specific for human Fas ligand (8 μg/ml, NOK-1, PharMingen) were added at the beginning of culture.

Example 2

Figure 4:
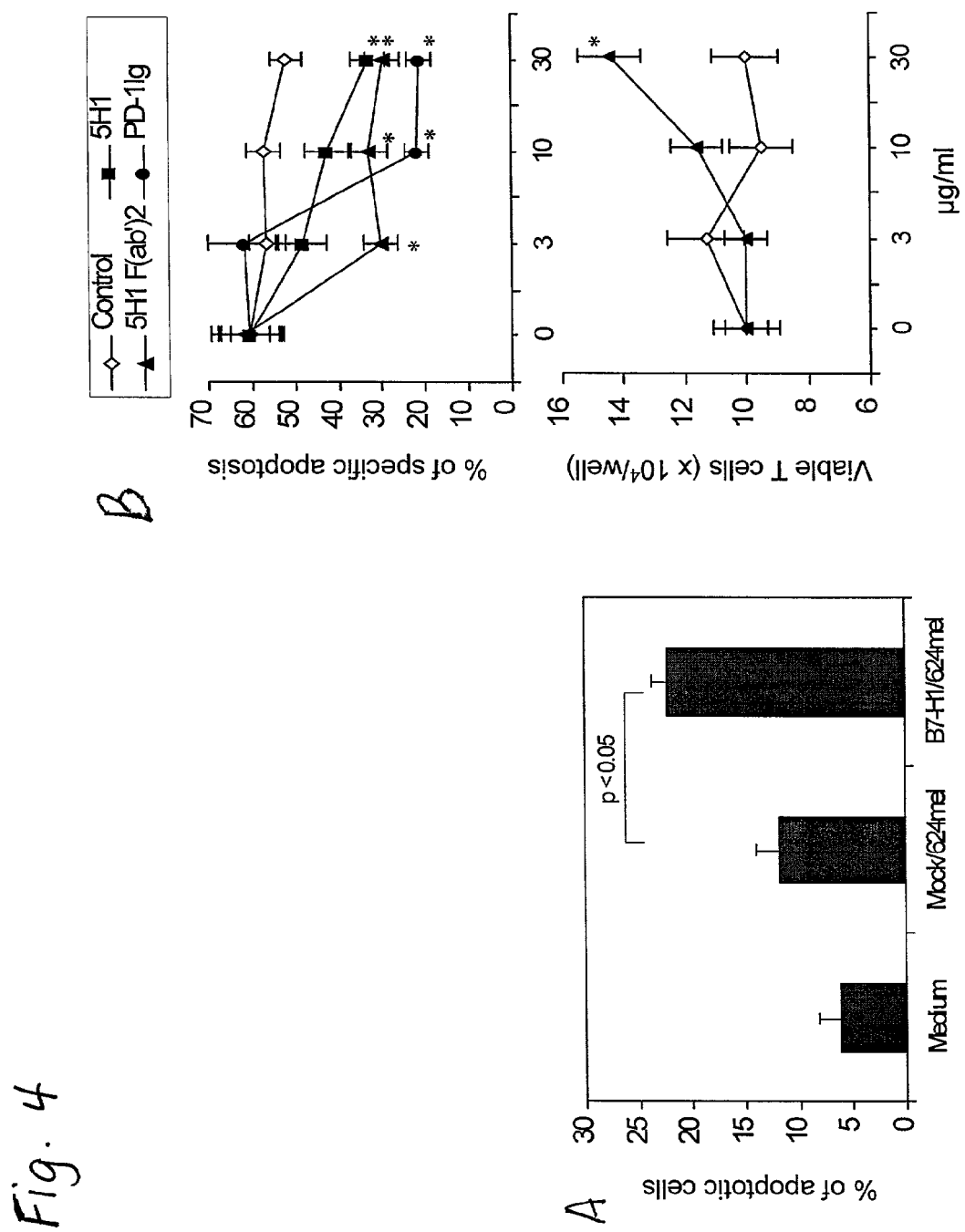
FIG. 4A is a bar graph showing the % of apoptotic cells recovered after 7 days from cultures containing cells of the CD8+ CTL clone M15 specific for a human melanoma peptide epitope alone (Medium) or with 624mel cells at a T cell to tumor cell ratio of 2:1. The 624mel cells used had been stably transfected with a control expression vector (Mock/624mel) or an expression vector containing a cDNA sequence encoding hB7-H1 (B7-H1/624mel). The cells were analyzed by FFC after Annexin V, CD4, and CD8 staining and the data are expressed as the % of cells staining with Annexin V and mAb specific for CD8 (AV+/CD8+).
FIG. 4B is a pair of line graphs showing the % of specific apoptosis (top graph) and the number of viable cells (bottom graph) in M15 cells after culture for 5 days with B7-H1/624mel cells in the presence of the indicated concentrations of control mouse Ig (Control), 5H 1 mAb specific for hB7-H1 (5H1), F(ab')$_2$ fragments of the 5H1 mAb (5H1 F(ab')2), or PD-1Ig fusion protein. Specific apoptosis was calculated as [(% apoptotic T cells in an experimental culture containing tumor cells and a blocking agent/% apoptotic cells in the control culture without tumor cells or blocking agent)−1]× 100. The apoptotic cells were detected by FFC as those staining with Annexin V and the viable cells were detected by trypan blue exclusion.

Activation of T Cells for an Extended Period of Time in the Presence of B7-H1 Enhances of Apoptosis of the T-Cells An immobilized fusion protein comprising the extracellular portion of hB7-H1 and the constant region of the heavy chain of human IgG1 (hB7-H1Ig) costimulated the growth of freshly isolated $CD3^+$ T cells from human peripheral blood mononuclear cells (PBMC) activated with a suboptimal TCR stimulus, i.e., with a low concentration of antibody specific for the CD3 molecule. Under such conditions, increased $^3$H-thymidine incorporation and the number of recovered viable cells indicated that the T cells proliferated for up to 64 hrs (FIGS. 1A and B). When the culture was continued for >88 hours, T cell proliferation decreased significantly in the presence of hB7-H1Ig, but continued in cultures that lacked hB7-H1Ig (FIGS. 1A and B). Annexin V (AV) and propidium iodide (PI) staining demonstrated accumulation of apoptotic T cells ($AV^+$ and $PI^-$) after 48 hrs of culture with B7-H1Ig (FIG. 1C). Thus, while hB7-H1Ig costimulated the growth of T cells in the initial phase, continued exposure of activated T cells to hB7-H1 inhibited T cell proliferation by enhancing apoptosis. Recent studies suggest that PD-1, an Ig superfamily molecule, is the receptor for hB7-H1 [Freeman (2000) J. Exp. Med. Vol. 192:1027-1034]. Inclusion of the PD-1Ig, fusion protein in the cultures however, did not block the effect of B7-H1 in either growth or death of T cells despite the capacity of PD-1Ig to bind to 624mel cells expressing transfected B7-H1 (FIG. 4D). It is possible thus that PD-1 is a low affinity receptor for B7-H1. The data indicate that ligation of B7-H1 with T cells induces a two-phase response, initially promoting growth of naive T cells and later resulting in apoptosis of activated T cells.

Example 3

Human Cancers But Not Normal Tissues Express hB7-H1

Monoclonal antibodies specific for hB7-H1 were used to determine whether hB7-H1 protein expression parallels of MRNA expression as previously determined. No hB7-H1 protein expression was detected in any normal solid tissue examined including breast, colon, pancreas, kidney, uterus, skeletal muscle, lung, liver, tonsil, and intestine. Interestingly, hB7-H1-expressing macrophages were observed in liver, lung and tonsil.

FFC analysis of tumor lines derived from a variety of human tissues demonstrated surface hB7-H1 expression on 4 of 9 lung carcinomas and 1 of 3 ovarian carcinomas (Table 1).

Surface expression of hB7-H1 was not detected on colonic or duodenal cell lines (n=4), leukemia (n=5), choriocarcinoma (n=2) or melanoma cell lines (n=6) (Table 1). However, when treated with IFN-γ, most non-expressing tumor lines were induced to express hB7-H1 (Table 1). Expression of hB7-H1 mRNA in these tumor cell lines was confirmed by the reverse transcriptase-coupled polymerase chain reaction (RT-PCR) using hB7-H1-specific primers (data not shown).

TABLE 1

Expression of hB7-H1 in human tumor cell lines

| Tissue origin | Cell line | Cancer Type | B7-H1 expression* Medium | B7-H1 expression* IFN-γ** |
|---|---|---|---|---|
| Lung | SK-LU-1 | Adenocarcinoma | − | − |
| | SK-MES-1 | Squamous carcinoma | + | ND |
| | NCI-H292 | Mucoepidemoid carcinoma | ++ | ND |
| | NCI-H128 | Small cell carcinoma | − | − |
| | NCI-H69 | Small cell carcinoma | − | − |
| | SCC-37 | Small cell carcinoma | − | + |
| | SCC-9 | Small cell carcinoma | − | − |
| | SCC-18 | Small cell carcinoma | + | + |
| | SCC-117 | Small cell carcinoma | ++ | ND |
| Ovary | CaOV3 | Adenocarcinoma | ++ | ND |
| | NIH-OVCAR3 | Adenocarcinoma | − | ND |
| | SK-OVCA3 | Adenocarcinoma | − | ++ |
| Colon | SW620 | Colorectal adenocarcinoma | − | + |
| | WiDr | Colorectal adenocarcinoma | − | + |
| | HT-29 | Colorectal adenocarcinoma | − | ++ |
| Duodenum | HuTu 80 | Adenocarcinoma | − | + |
| Leukemia/ lymphoma | U937 | Monocyte | − | + |
| | K562 | Erythromyeloblast | − | − |
| | Jurkat | T lymphocyte | − | − |
| | Molt 4 | T lymphocyte | − | ND |
| | Raji | B lymphocyte | − | + |
| Placenta | JAR | Choriocarcinoma | − | + |
| | Bewo | Choriocarcinoma | − | − |
| Skin | SK-MEL-28 | Melanoma | − | ++ |
| | HT-144 | Metastatic melanoma | − | + |
| | 624 mel | Melanoma | − | − |
| | 697 mel | Melanoma | − | − |
| | 888 mel | Melanoma | − | − |
| | 586 mel | Melanoma | − | + |

*The expression of B7-H1 was determined by FACS analysis using anti-hB7-H1 mAb.
++: >50% positive;
+: 10-50% positive;
−: <10% positive;
ND: not done.
**Cells were incubated with 2,000 IU/ml of recombinant human IFN-γ for 24-48 hours before FACS analysis Immunohistochemical analysis demonstrated hB7-H1 expression in a majority of freshly isolated human lung carcinomas (20/21 patients), ovarian carcinomas (20/23 patients), colon carcinomas (10/19 patients) and melanomas (22/22 patients) (summarized in Table 2). B7-H1 expression was observed in the plasma membrane, cytoplasm or both. hB7-H1 expression was usually focal with adjacent normal tissues negative. hB7-H1 was evident on metastatic melanoma cells residing in lymph nodes, but not on adjacent lymphocytes.

TABLE 2

Expression of hB7-H1 in human cancer tissues

| Diagnosis | Specimen numbers Positive/Total (%) | Staining Intensity* | | | |
|---|---|---|---|---|---|
| | | − | + | ++ | +++ |
| Lung Cancer | 20/21 (95) | 1 | 9 | 10 | 1 |
| Adenocarcinoma | 10/10 | 0 | 5 | 5 | 0 |
| Squamous cell carcinoma | 8/8 | 0 | 2 | 5 | 1 |
| Large cell carcinoma | 1/2 | 1 | 1 | 0 | 0 |
| Neuroendocrine carcinoma | 1/1 | 0 | 1 | 0 | 0 |
| Ovarian Cancer | 20/23 (87) | 3 | 8 | 11 | 1 |
| Adenocarcinoma | 19/22 | 3 | 7 | 11 | 1 |
| Carcinosarcoma | 1/1 | 0 | 1 | 0 | 0 |
| Melanoma | 22/22 (100) | 0 | 5 | 12 | 5 |
| Skin | 13/13 | 0 | 4 | 6 | 3 |
| Lymph node metastasis | 5/5 | 0 | 0 | 4 | 1 |
| Brain metastasis | 1/1 | 0 | 0 | 1 | 0 |
| Axilla metastasis | 2/2 | 0 | 1 | 0 | 1 |
| Breast metastasis | 1/1 | 0 | 0 | 1 | 0 |
| Colon Adenocarcinoma | 10/19 (53) | 9 | 6 | 2 | 2 |

*Intensity of staining by anti-hB7-H1 mAb: −, negative; +, focal expression in 10-40% of the cancer tissues; ++, focal expression in 40-80% of the cancer tissues, +++, diffuse expression in >80% of the cancer tissues.

Example 4

B7-H1 on Tumor Cells Enhances Apoptosis of T Cells that Respond to Tumor Antigens on the Tumor Cells

Figure 2:
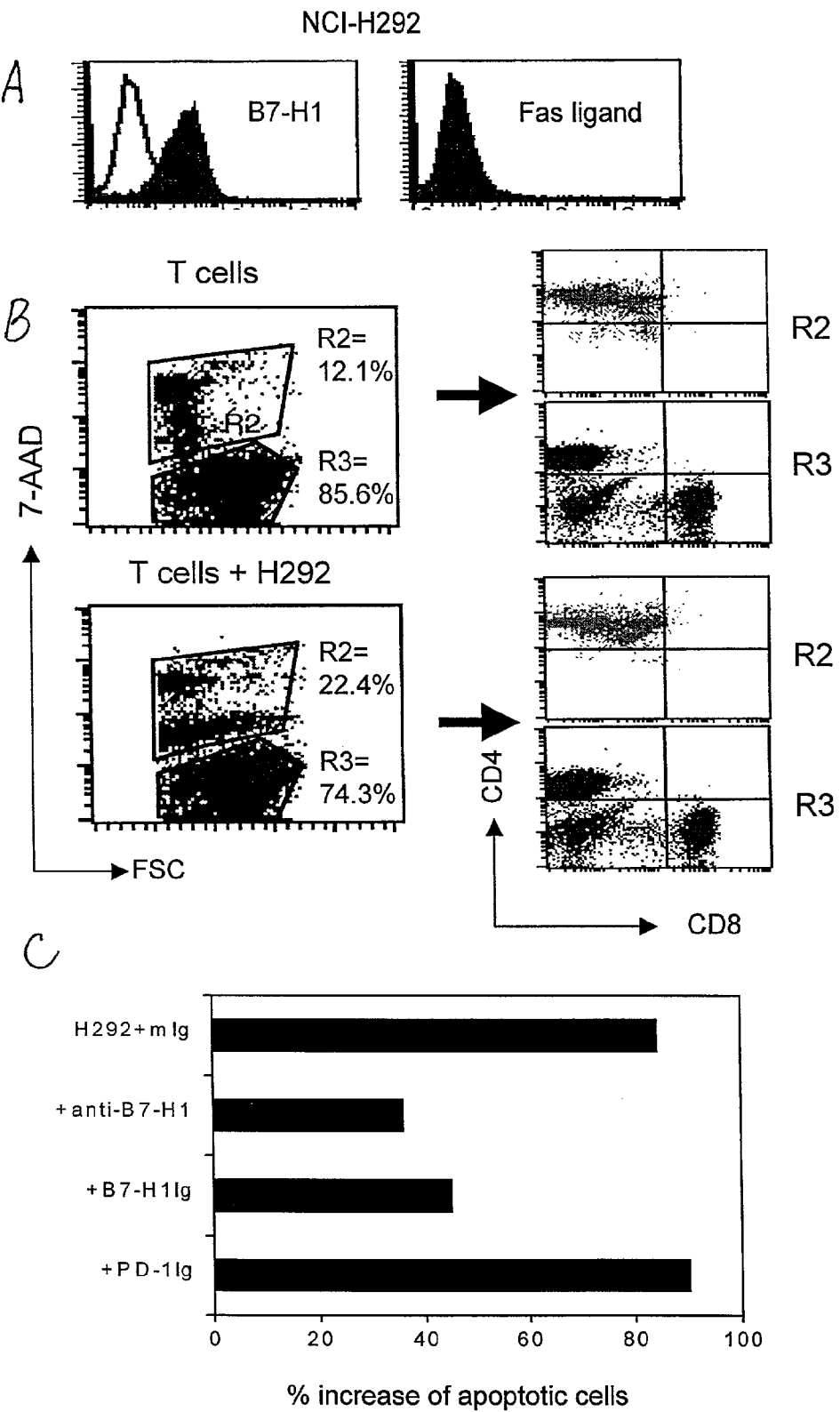
FIG. 2A is a pair of FFC histograms showing the expression of hB7-H1 (B7-H1) and lack of expression of Fas ligand by cells of the NCI-H292 human lung carcinoma cell line. The cells were stained with antibody specific for hB7-H1 (left histogram) or Fas ligand (right histogram) and fluorescein isothiocyanate- (FITC-) conjugated F(ab')$_2$ goat anti-mouse IgG antibody (filled profiles) or with FITC-conjugated F(ab')$_2$ goat anti-mouse IgG antibody only (unfilled profiles).
FIG. 2B is series of six two-dimensional FFC histograms of purified human T cells that had been cultured (2×10$^5$ per well) alone (T cells) or with irradiated NCI-H292 cells (4×10$^4$ per well) (T cells+H292) for 5 days and then stained with 7-AAD, anti-CD4, and anti-CD8 antibody. The histograms on the right show the data in terms cells of staining with 7-AAD and forward light scatter (FSC) which is a function of cell size; the R2 (apoptotic cells) and R3 gates (live cells) are indicated. The cells in R2 and R3 gates were then analyzed for their expression of CD4 and CD8 and the relevant data are shown in the four two-dimensional FFC histograms on the right.
FIG. 2C is a bar graph showing the % increase of apoptotic cells when 20 μg/ml of either soluble 2H11 mAb specific for hB7-H1 (anti-B7-H1), soluble PD-1Ig fusion protein (PD-1Ig), soluble hB7-H1Ig fusion protein (B7-H1Ig), or soluble control mouse IgG were added to cultures containing purified human T cells and NCI-H292 cells (as described for FIG. 2A). The apoptotic cells were detected by staining with 7-AAD.

In light of the above findings, it seemed possible that deletion of antigen-specific T cells could represent a mechanism for tumor cells to evade immune destruction. To test this possibility, T cells were purified from peripheral blood mononuclear cells of healthy donors and incubated for 5 days with irradiated cells of the NCI-H292 line, a hB7-H1$^+$ FasL$^-$ mucoepidermoid lung carcinoma cell line (FIG. 2A). T cells undergoing apoptosis were detected by triple staining with 7-amino-actinomycin D (7-AAD) and CD4 and CD8-specific mAbs to identify the subsets of apoptotic T cells. Staining of unfixed cell preparations with 7-AAD allows unstained live cells to be discriminated from early-stage apoptotic cells and from cells with compromised membrane integrity (late apoptotic or necrotic cells). FIG. 2B shows that 22.4% of T cells were apoptotic (7-AAD$^+$) in cultures containing NCI-H292 cells, while only 12.1% of T cells were apoptotic when cultured with medium only. This difference represented an increase of 85% in apoptotic T cells over the basal level. CD4$^+$ T cells accounted for >95% of apoptotic T cells while the viable population contained both CD4$^+$ and CD8$^+$ cells (FIG. 2A). Importantly, inclusion of anti-B7-H1 mAb or soluble hB7-H1Ig fusion protein in the culture resulted in significant inhibition of apoptosis (>50% (P<0.05)). Inclusion of PD-1Ig did not prevent apoptosis (FIG. 2C).

Figure 3:
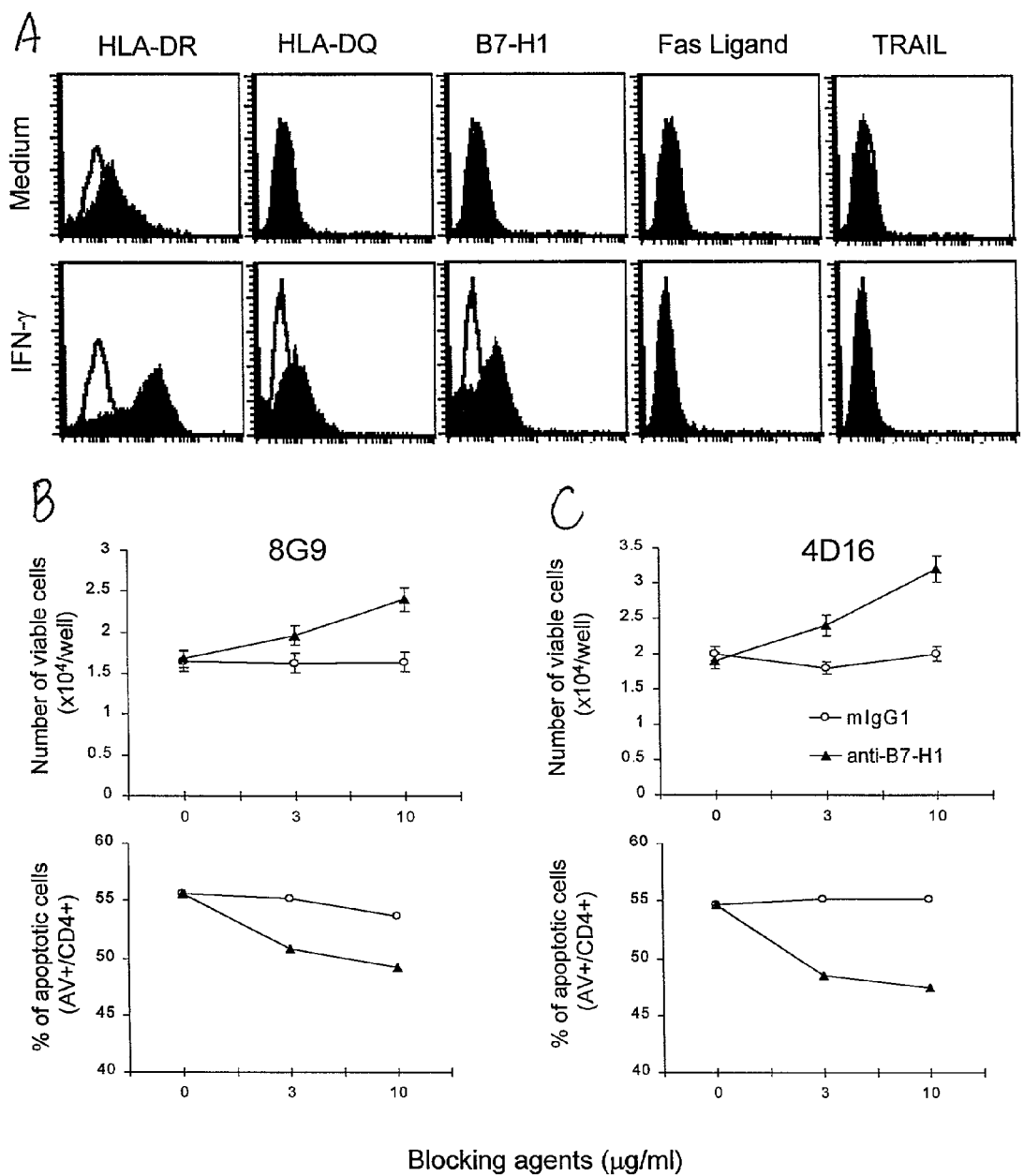
FIG. 3A is a series of ten FFC histograms showing the expression (or lack of expression) of HLA-DR, HLA-DQ, B7-H1, Fas Ligand, and TRAIL by cells of the Skel-28 human melanoma cell line that had been cultured in medium alone (Medium) or in medium containing interferon-γ (IFN-γ). Cells stained with antibodies specific for the listed cell-surface molecules are indicated by filled profiles and those stained with a control antibody (mouse IgG1) are indicated by unfilled profiles.
FIGS. 3B and C are four line graphs showing the number of viable cells (top graphs) and the % apoptotic cells (bottom graphs) recovered from cultures of IFN-γ treated Skmel-28 cells (2×10$^4$ per well) and cells of the melanoma peptide-epitope specific 8G9 CD4+ T cell clone (FIG. 3B) (2×10$^5$ per well) or cells of the alloantigen-specific 4D16 CD4+ T cell clone (2×10$^5$ per well) after 6 days of culture. The cultures also contained as blocking agents (at the indicated concentrations) either 2H11 mAb specific for hB7-H1 (anti-B7-H1) or control mouse IgG$_1$ (MIgG1). The cultures containing the 8G9 cells also contained the melanoma (MAGE-3) peptide eiptope (10 μg/ml).
FIG. 3D is a series of four FFC histograms showing the expression of hB7-H1 by cells of the 624mel human melanoma cell line that had been stably transfected with a control expression vector (left histograms) or an expression vector containing a cDNA sequence encoding hB7-H1 (right histograms). The cells were stained with either a mAb specific for hB7-H1 (Anti-B7-H1) (top histograms; filled profiles), PD-1Ig fusion protein (bottom histograms; filled profiles), or control antibody (mouse IgG1; unfilled profiles).
Figure 3D:
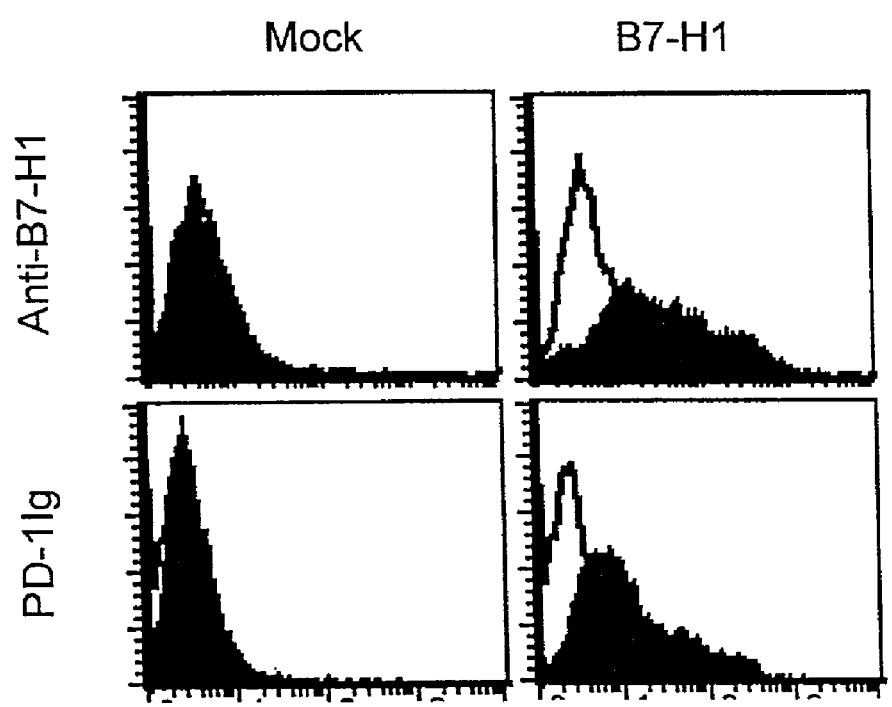

In order to confirm that hB7-H1 on tumor cells promotes apoptosis of T cells, cells of the hB7-H1-non-expressing human melanoma line, 624mel, were transfected with a plasmid encoding full-length hB7-H1 cDNA. hB7-H1 expression on transfected cells (B7-H1/624mel) was confirmed by staining with anti-hB7-H1 mAb (FIG. 3D). After purified human T cells had been co-cultured for 6 days with 624mel cells, there were significantly more apoptotic cells than when the same T cells were cultured under the same conditions with mock-transfected 624mel cells (data not shown). Taken together, these results indicate that tumor-associated hB7-H1 promotes apoptosis of T cells.

The increased apoptosis in T cells after prolonged exposure to tumor-associated hB7-H1 in the above experiments could have been due to allogeneic antigen rather than tumor antigen recognition by T cells. To investigate whether T cells specific for tumor antigens respond similarly to tumor-associated hB7-H1, induction of apoptosis in the 8G9 CD4$^+$ human T cell clone, which recognizes an HLA-DR4-restricted helper T cell epitope of tumour antigen MAGE-3$_{146-160}$, was tested. The MAGE-3$^+$ human melanoma line, SKmel-28, expresses a low level of HLA-DR4 that is upregulated by treatment with IFN-γ. IFN-γ treatment of SKmel-28 also upregulated hB7-H1 and HLA-DQ but not Fas ligand or TRAIL (FIG. 3A). IFN-γ treated SKmel-28 cells stimulates cells of the 8G9 T cell clone to release GM-CSF (data not shown). Incubation of 8G9 T cell clone with IFN-γ treated Skmel-28 cells for 6 days led to a reduced number of viable cells and an increase in apoptotic T cells (50-55%). Inclusion of anti-hB7-H1 mAb in the 6-day culture significantly reduced apoptosis and increased survival of T cells (FIG. 3B). Similar results were obtained with another CD4$^+$ T cell clone, 4D16 (FIG. 3C), that recognizes HLA-DQ8 allogeneic antigens expressed on SKmel-28 cells.

Example 5

Tumor-Associated hB7-H1 Increases Anoptosis of Antigen-Specific Human T Cells

Figure 5:
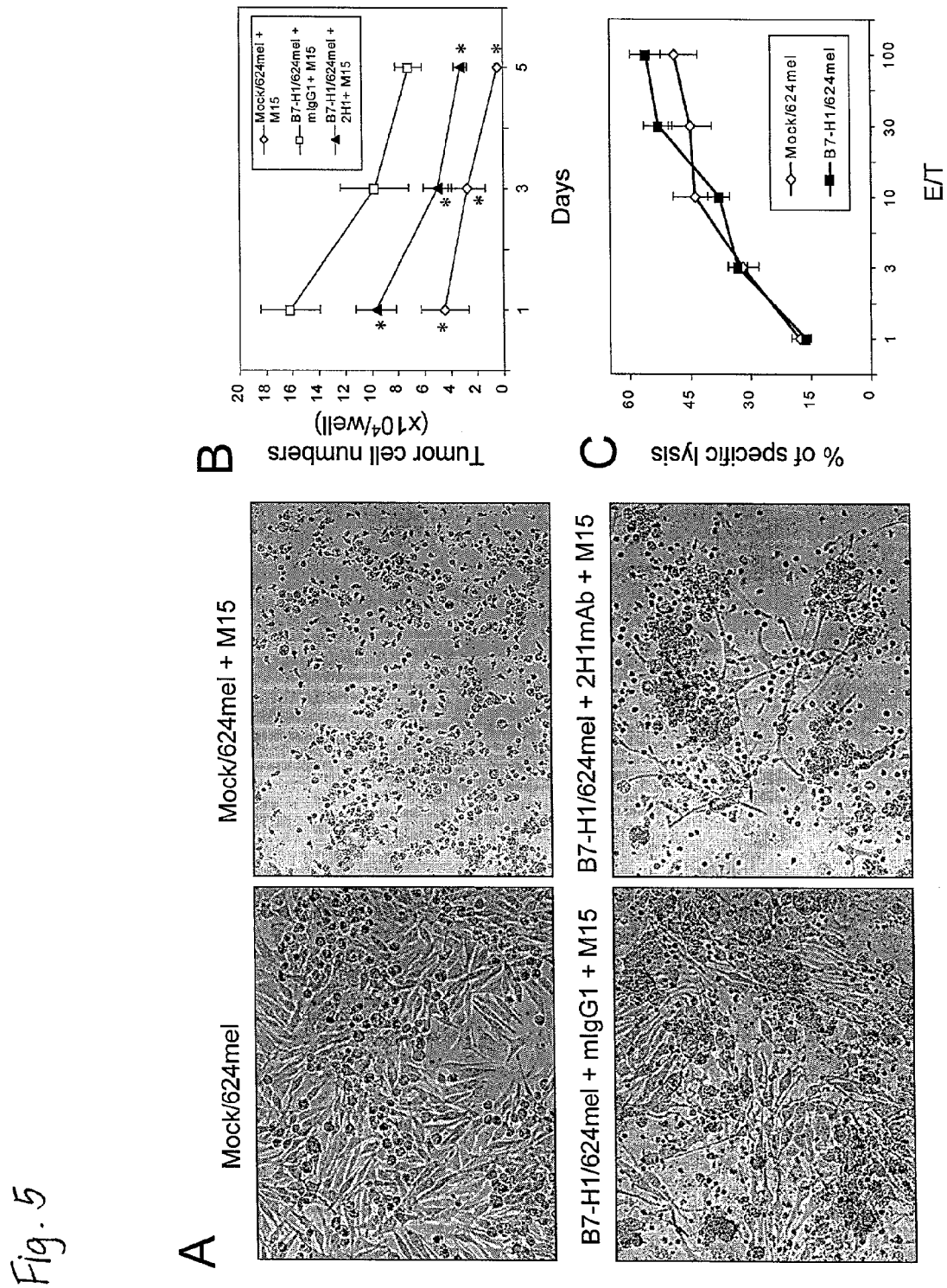
FIG. 5A is a series of photomicrographs of Mock/624mel cells (top panels) or B7-H1/624mel cells (bottom panels) that has been cultured for 5 days with medium only (top left panel), M15 cells (top right panel), M15 cells and control mouse IgG1 (10 μg/ml; bottom left panel), or M15 cells and 2H1 mAb specific for hB7-H1 (10 μg/ml; bottom right panel). The cultures initially contained 3×10$^5$ tumor cells per well and those cultures containing M15 cells contained the same number of M15 cells.
FIG. 5B is a line graph showing the number of viable Mock/624mel cells or B7-H1/624mel cells (detected by trypan blue exclusion) recovered after various times of culture in the presence of M15 cells only, M15 cells and control mouse IgG1 (mIgG1), or 2H1 mAb. Culture conditions were as described for FIG. 5A. Asterisks indicated data points that are significantly different (P<0.05) from corresponding data points obtained from cultures containing B7-H1/624mel cells, M15 cells, and mIgG1.
FIG. 5C is a line graph showing the level of cytolysis (% specific lysis as measured in a standard $^{51}$Cr release assay) of Mock/624mel cells and B7-H1/624mel cells after incubation with M15 cells for 4 hours at the indicated M15 cell to tumor target cell ratios (E/T).

To determine the effect of tumor-associated B7-H1 on CD8+ T cells, B7-H1/624mel cells were again used. Parental, untransfected 624mel cells express the gp100 tumor antigen and MHC class I molecules (HLA-A2), [Rivoltini et al. (1995), Cancer Res. 55:3149-3157] but not hB7-H1, even after treatment with IFN-γ (FIG. 3D and Table 1). In addition, 624mel cells do not express Fas ligand (FasL) or TRAIL proteins, which are known to participate in the induction of T cell apoptosis [Nagata et al. (1995) Science 267:1449-1456; Jeremias et al. (1998) J. Immunol. 28:143-152; Zhao et al. (1999) Br. J. Haematol. 106:827-832]. A human CD8$^+$ cytolytic T cell (CTL) clone (M15) specific for a gp100 peptide epitope was generated from peripheral blood mononuclear cells obtained from a healthy HLA-A2-expressing donor by a previously described method involving repeated stimulation in vitro with the HLA-A2-restricted gp100 epitope peptide [Lu et al. (2000) Cancer Res. 60:5223-5227]. This gp100 peptide-reactive clone specifically lyses gp100+ tumor cells (FIG. 5C and unpublished data). M15 CTL were co-cultured with irradiated B7-H1/624mel cells or mock-transfected 624mel cells (Mock/624mel) and T cell apoptosis was assessed by double staining with Annexin V and anti-CD8 mAbs. FIG. 4A shows that when M15 CTL were co-cultured with Mock/624mel cells for 5 days, 14±5.6% of the M15 CTL cells underwent apoptotic death. However, when co-cultured with B7-H1/624mel cells, 23±4.7% of the M15 CTL population underwent apoptotic death (FIG. 4A). This represented a relative increase of 62% (P<0.05). The ligand specificity of this phenomenon was demonstrated by including in the culture medium anti-hB7-H1 mAb or F(ab')$_2$ fragments of the mAb. The anti-hB7-H1 mAb inhibited apoptosis of T cells by >50% (P<0.05) and increased the number of viable T cells 1.4-fold (P<0.05). Addition of PD-1Ig fusion protein at high concentrations also significantly inhibited the induction of M15 cell apoptosis by B7-H1/624mel (FIG. 4C). Consistent with this observation, nearly all Mock/624mel cells were eliminated in 5-day cultures with M15 CTL while B7-H1/624mel target cells were unaffected. Inclusion of anti-hB7-H1 mAb in the cultures abrogated the resistance of B7-H1/624mel cells to killing by T cells (FIGS. 5A and B).

To exclude the possibility that the resistance of B7-H 1/624mel cells to M15 CTL may have been due to decreased lysis of B7-H1/624mel rather than to inhibition of M15 CTL proliferation, the sensitivity of Mock/624mel and B7-H1/624mel cells to M15-mediated lysis was compared in a 4-hour $^{51}$Cr release cytotoxicity assay. As shown in FIG. 5C, Mock/624mel and B7-H1/624mel were equally sensitive to the lysis by M15 CTL. In addition, there was no growth advantage of B7-H1/624mel over Mock/624mel cells in a proliferation assay in vitro (data not shown). These results support the conclusion that the deletion of M15 CTL by exposure to hB7-H1 is responsible for the outgrowth of B7-H1/624mel cells.

Figure 6:
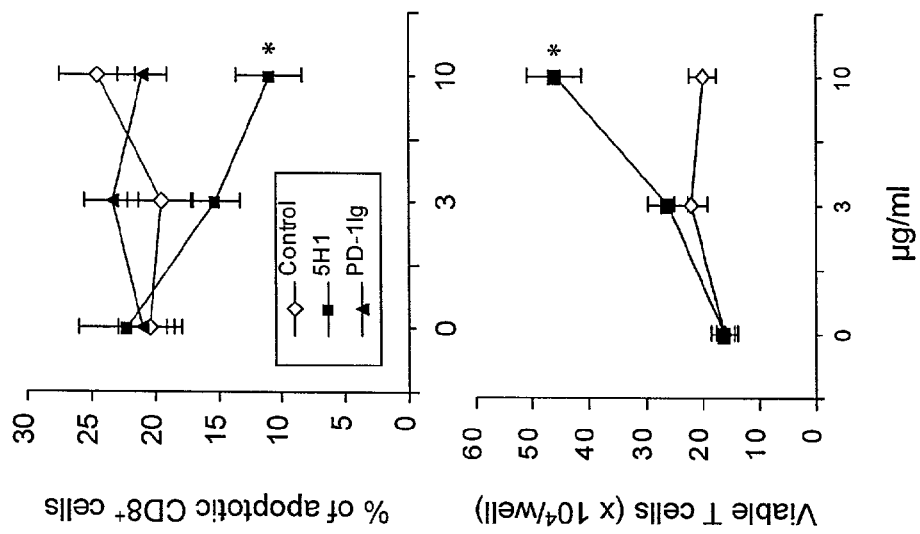
FIG. 6A is a series of four FFC histograms showing: the expression by cells of the human breast carcinoma cell line HBL-100 of hB7-H1 as detected by staining with the 5H1 mAb specific for hB7-H1 (top left histogram) and the PD-1Ig fusion protein (top right histogram); and the lack of expression of Fas ligand and TRAIL as detected by staining with mAbs specific for the two cell surface markers (Anti-FasL and Anti-TRAIL, respectively). Fluorescence obtained by staining with the test reagents is shown by the filled profiles and staining obtained with control mAb is shown by unfilled profiles.
FIG. 6B is a pair of line graphs showing the % of apoptotic cells in the CD8+ cells (top graph) and the concentration of viable cells (bottom graph) in T cells recovered from cultures of HBL-100 cells and cells of the M99 CD8+ CTL clone M99 that is specific for a carcinoembryonic antigen (CEA) peptide epitope. The cultures also contained either no blocking agent (Control), the 5H1 mAb specific for hB7-H1 (5H1) or the PD-1Ig fusion protein (PD-1Ig). Apoptotic CD8+ cells and viable cells in recovered T cells were detected by FFC after staining with Annexin V and antibody specific for human CD8 and FFC and by trypan blue exclusion, respectively.
Figure 6:
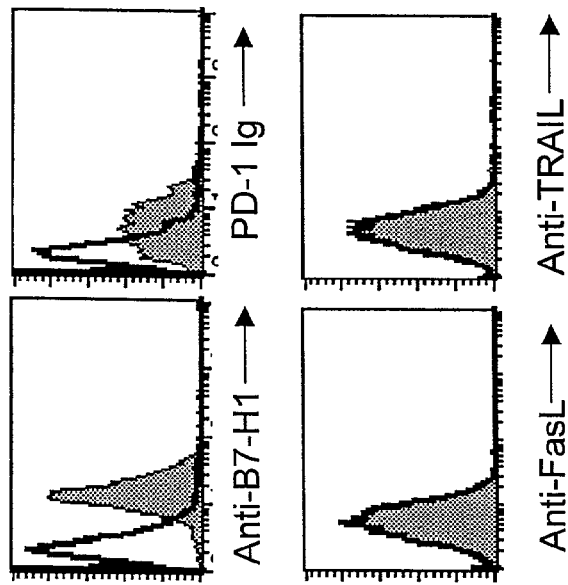

The ability of cells of HBL-100 (a human breast cancer line) that constitutively express hB7-H1 on their surfaces to induce T cell apoptosis was tested. FIG. 6A demonstrates that HBL-100 cells express hB7-H1, but do not express FasL or TRAIL on their surfaces (FIG. 6A). HBL-100 cells express a CTL epitope (IPQQHTQVL) (SEQ ID NO: 2) that is derived from carcinoembryonic antigen (CEA), is HLA-B7-restricted, and is recognized and lysed by CD8+ CTL clone M99 [Lu et al. (2000) Cancer Res. 60:5223-5227]. As observed with B7-H1/624mel cells, the number of antigen-specific M99 CTL was reduced and apoptosis increased when they were incubated with HBL-100 cells. T cell death was inhibited when anti-B7-H1 mAb was included in the medium (FIG. 6B). The addition of PD-1Ig (at up to 10 μg/ml) did not inhibit the apoptosis of T cells induced by HBL-100 cells. These data provide further evidence that hB7-H1 expression on tumor cells causes apoptosis of tumor antigen-specific T cells in vitro.

Figure 7:
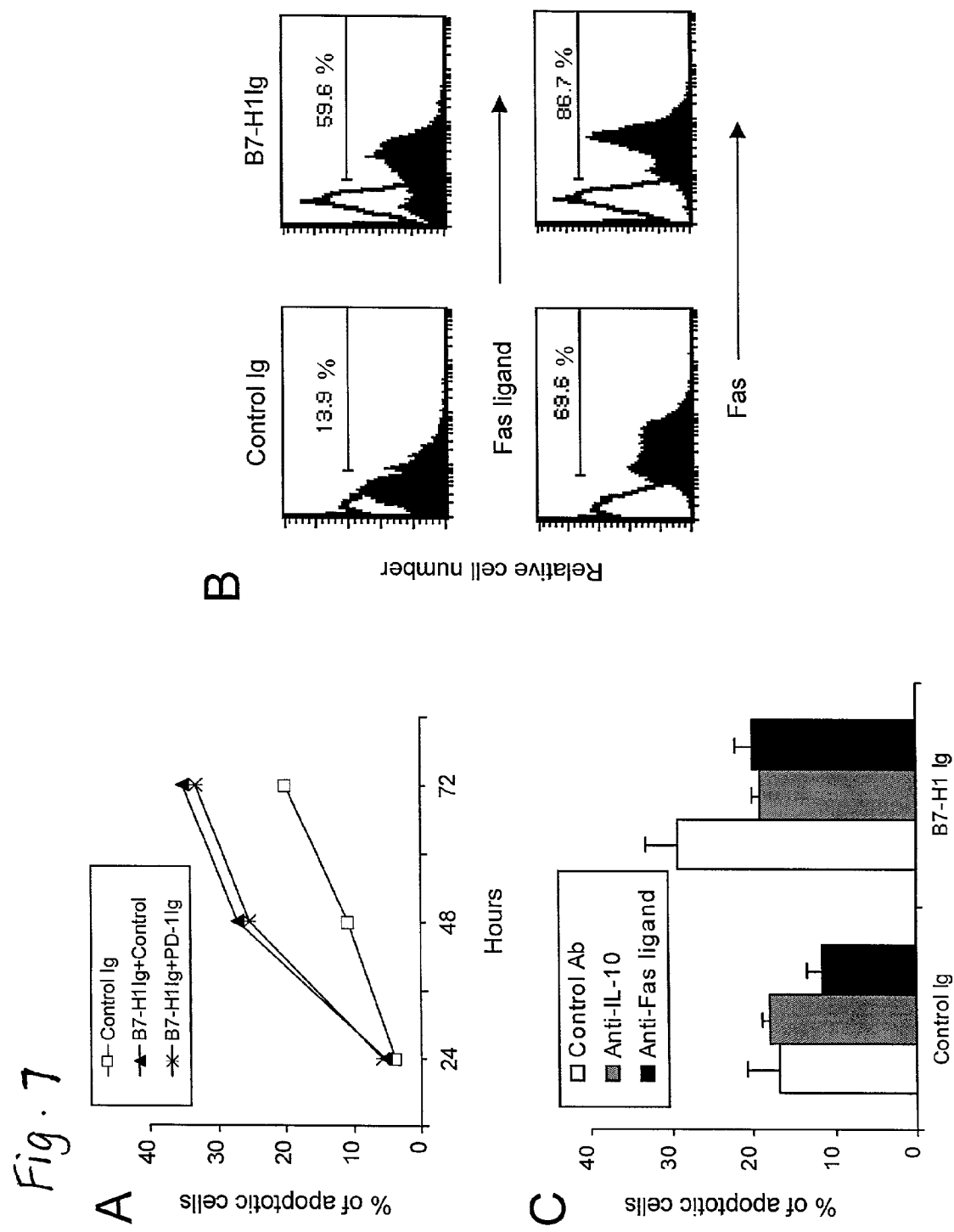
FIG. 7A is a line graph showing the % of apoptotic cells in cells recovered at various times from cultures of purified human T cells ($2\times10^5$ per well) and plate bound hB7-1Ig fusion protein (or control Ig) each coated onto the tissue culture plates at a concentration of 10 µg/ml and plate bound mAb specific for human CD3 coated onto the plates at an optimal dose (1 µg/ml). Some of the wells also contained as blocking agents either soluble PD-1Ig fusion protein or soluble control Ig, each at concentration of 30 µg/ml. Apoptotic cells were detected by FFC as cells staining with FITC-Annexin but not staining with PI.
FIG. 7B is a series of four FFC histograms showing the expression of Fas ligand (top histograms) and Fas (bottom histograms) on cells recovered at 72 hours from the cultures described for FIG. 7A. Cells from only the cultures without blocking agents were tested. Cells stained with a FITC-conjugated mAb specific for Fas ligand (bottom histograms) or a mAb specific for Fas ligand and FITC-conjugated goat F(ab')$_2$ anti-mouse IgG (top histograms) are indicated by the filled profiles and those stained with control antibodies are indicated by unfilled profiles. The bars indicate the gating used to estimate the percentages % of cells expressing either Fas ligand or Fas and these percentages are shown above the bars.
FIG. 7C is a bar graph showing the % of apoptotic cells in cells recovered at 72 hours from the cultures described for FIG. 7A. However, instead of PG-1Ig fusion protein or control Ig, some of the cultures of the present experiment contained as blocking agents soluble neutralizing mAb specific for either interleukin-10 (Anti-IL10) or Fas ligand (Anti-Fas ligand) or a control antibody (Control Ab). Apoptotic cells were detected as described for the experiment shown in FIG. 7A.

To dissect the mechanisms of B7-H1-mediated apoptosis, an in vitro human T cell culture system was employed. Immobilized B7-H1Ig and an optimally activating dose of immobilized anti-CD3 mAb rapidly induced apoptosis of purified human T cells 48 hrs after initiation of the cultures (FIG. 7A). Apoptosis of T cells was significantly blocked by anti-hB7-H1 mAb (data not shown) but not by PD-1Ig (FIG. 7A). Upon stimulation by anti-CD3 and hB7-H1Ig, expression of Fas and Fas ligand (FasL) were upregulated in activated T cells (FIG. 7B). In addition, secretion of IL-10 in hB7-H1Ig-containing cultures increased dramatically [Dong et al. (1999) Nature Med. 5:1365-1369]. Since both Fas-FasL and IL-10 are involved in the activation-induced cell death of T cells [Nagata et al. (1995) Science 267:1449-1456; and Georgescu et al. (1997) J. Clin. Invest. 100:2622-2633], the role of these molecules in hB7-H1-mediated apoptosis was investigated. As shown in FIG. 7C, inclusion of anti-FasL mAb partially blocked the apoptosis induced by anti-CD3 mAb without hB7-H1Ig while anti-IL-10 mAb did not. However, apoptosis of T cells induced by anti-CD3 mAb and hB7-H1Ig was inhibited to the level of apoptosis induced by anti-CD3 without hB7-H1Ig by both anti-FasL or anti-IL-10 mAbs, but was not inhibited by control mAb (FIG. 7C). These results indicate that the Fas/FasL interaction and IL-10 are involved, at least in part, in hB7-H1-induced apoptosis of activated T cells.

Example 6

Tumor-Associated mB7-H1 Deletes Activated Antigen-Specific T Cells In Vivo

Figure 8:
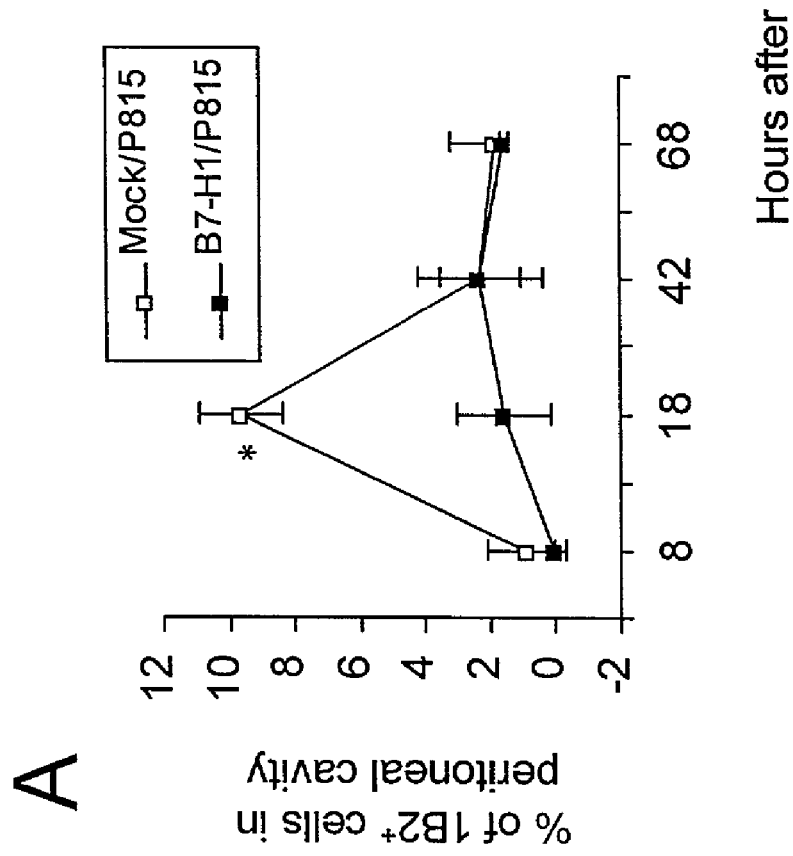
FIGS. 8A and B are line graphs showing the % of cells expressing the 2C transgenic T cell receptor (TCR) (IB2$^+$ cells.

To determine whether T cell apoptosis in vitro is a correlate of activated T cell deletion in vivo, a mouse model involving adoptive transfer of 2C T cell receptor (TCR) transgenic mouse T cells which recognize a p2Ca peptide in the context of $L^d$ MHC class I molecule on the P815 tumor line [Sykulev et al. (1994) Proc. Natl. Acad. Sci. USA 91:11487-11491] was used. Mock-transfected P815 cells (Mock/P815) or P815 cells transfected with a vector that expressses mB7-H1 (B7-H1/P815) were injected intraperitoneally (i.p.) into immuno-deficient RAG-1$^{-/-}$ mice to establish progressively growing tumors. 2C T cells were activated by incubation in vitro with BALB/c (H-2$^d$) spleen cells in the presence of human IL-2 and then transferred i.p. into the P815-bearing mice. By 18 hours after initial contact with the tumor cells, the relative proportion of 2C T cells had greatly increased in mice harboring Mock/P815 cells and accounted for nearly 10% of total peritoneal cells. This increase in the number of 2C T cells was not seen in mice injected with B7-H1/P815 cells (FIG. 8A). Furthermore, 2C T cells in mice harboring B7-H1/P815 tumor cells had, by 8 hrs after transfer, undergone significant apoptosis compared to mice injected with Mock/P815 tumor cells (FIG. 8B). The level of apoptotic cells decreased by 42 hrs. The lack of 2C T cell expansion in B7-H1/P815-bearing mice attested to the ligand specificity of the 2C T cell population's initial expansion in mice bearing mock/P815 cells. The rapid increase in T cell apoptosis after being exposed for 18 hrs to mB7-H1-transfected tumor cells provides evidence of in vivo deletion of activated T cells by tumor-associated B7-H1.

What is claimed is:

1. A method of inhibiting tumor cell proliferation in a subject, comprising:
   (a) identifying a subject with cancer; and
   (b) administering to the subject an antibody that binds to B7-H1.

2. The method according to claim 1, wherein cells of the cancer are identified as expressing B7-H1 molecules on their surfaces.

3. The method according to claim 1, wherein said B7-H1 comprises the amino acid sequence set forth in SEQ ID NO: 3.

4. The method according to claim 1, wherein said antibody interferes with an interaction between the T cell and B7-H1.

5. The method according to claim 1, wherein said subject is a human.

6. The method according to claim 1, wherein said subject is a mouse.

7. The method of claim 1, wherein the cancer is a hematological cancer, a neurological cancer, breast cancer, a gastrointestinal cancer, or a genitourinary cancer.

8. The method of claim 7, wherein the gastrointestinal cancer is colon cancer.

9. The method of claim 7, wherein the genitourinary cancer is ovarian cancer.

10. The method of claim 1, wherein the cancer is melanoma.

11. The method of claim 1, wherein the cancer is lung cancer.

12. The method of claim 1, wherein the cancer is head and neck cancer, liver cancer, pancreatic cancer, bone cancer, or a vascular cancer.

13. The method of claim 1, wherein the antibody is a monoclonal antibody.

14. The method of claim 1, wherein the antibody is a polyclonal antibody.

15. The method of claim 1, wherein the antibody is an antigen-binding fragment.

16. The method of claim 15, wherein the antigen-binding fragment is a single chain Fv fragment.

17. The method of claim 1, wherein the antibody is a chimeric antibody.

18. The method of claim 1, further comprising delivering one or more cytokines to the subject.

19. The method of claim 1, further comprising administering an immunogenic stimulus to the subject.

20. The method of claim 19, wherein the immunogenic stimulus comprises a tumor-associated antigen.

* * * * *